(12) United States Patent
Li et al.

(10) Patent No.: US 6,808,887 B2
(45) Date of Patent: Oct. 26, 2004

(54) USES OF KU70

(75) Inventors: Gloria C. Li, New York, NY (US); Carlos Cordon-Cardo, New York, NY (US); Honghai Ouyang, West Windsor, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/161,025

(22) Filed: Jun. 3, 2002

(65) Prior Publication Data

US 2003/0096262 A1 May 22, 2003

Related U.S. Application Data

(62) Division of application No. 09/343,634, filed on Jun. 30, 1999, now Pat. No. 6,399,298.
(60) Provisional application No. 60/091,188, filed on Jun. 30, 1998.

(51) Int. Cl.[7] .............................. C12Q 1/68; C12Q 1/00
(52) U.S. Cl. ................. 435/6; 435/4; 435/7.1; 435/183; 435/455; 436/94
(58) Field of Search .................. 435/6, 4, 7.1, 183, 435/455; 436/94

(56) References Cited

U.S. PATENT DOCUMENTS 6,001,882 A * 12/1999 Fox et al. .................. 514/680
6,200,754 B1 * 3/2001 Housman et al. .............. 435/6

* cited by examiner

Primary Examiner—Carla J. Myers
(74) Attorney, Agent, or Firm—John P. White; Cooper & Dunham LLP

(57) ABSTRACT

This invention provides a method of diagnosing a predisposition to cancer in a subject comprising: (a) obtaining a nucleic acid sample from the subject; and; (b) determining whether one or more of the subject's Ku70 alleles or regulatory regions to those alleles are deleted or different from the wild type so as to reduce or eliminate the subject's expression of polypeptide having tumor suppressor activity. This invention also provides a method of assessing the severity of cancer in a subject comprising: (a) obtaining a nucleic acid sample from the subject; and (b) determining whether one or more of the subject's Ku70 alleles or regulatory regions to those alleles are deleted or different from the wild type so as to reduce or eliminate the subject's expression of polypeptide having tumor suppressor activity. This invention also provides a method of assessing the severity of cancer in a subject comprising: determining the subcellular localization of Ku70 in the subject, wherein an abnormal subcellular localization of Ku70 indicates a predisposition to cancer.

2 Claims, 24 Drawing Sheets

Thy

Spl

LN wild type (HE)

Ku80-/- (HE)

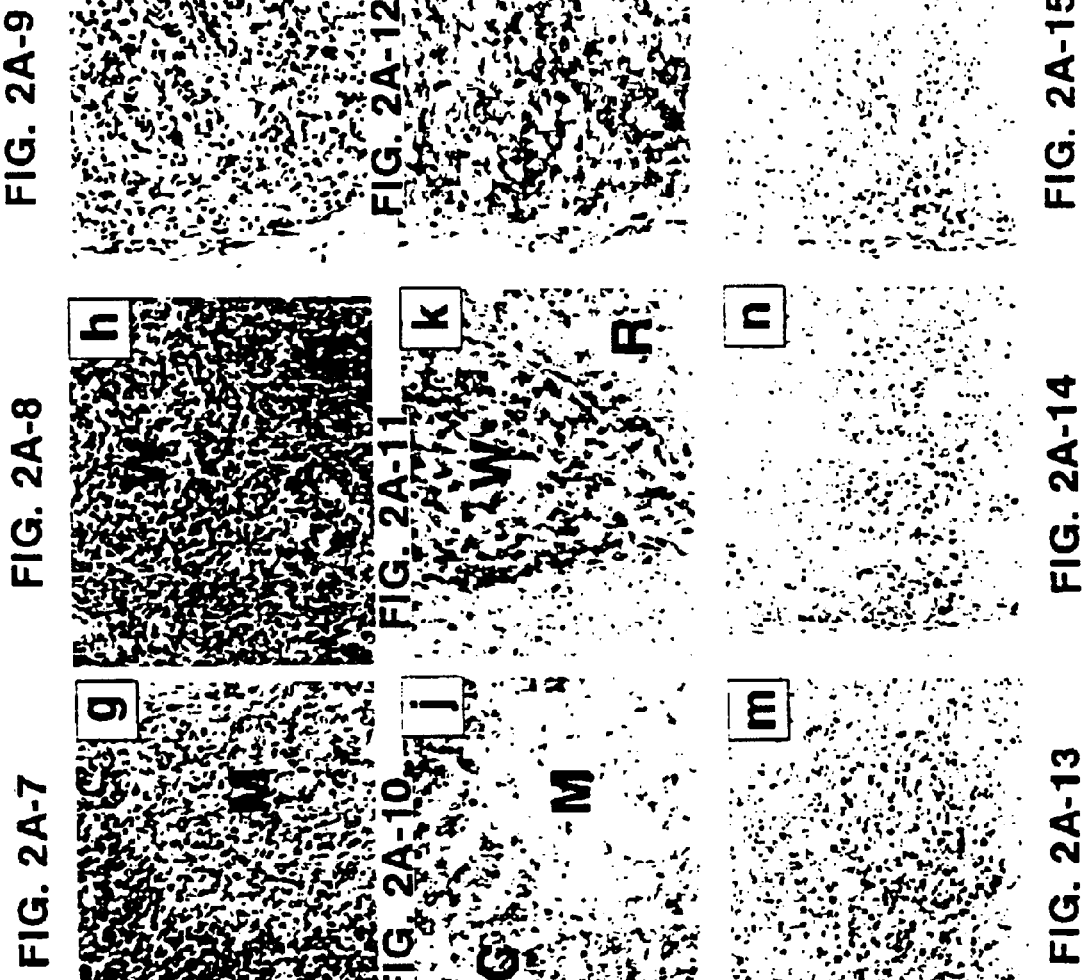

FIG. 2B-1    FIG. 2B-2    FIG. 2B-3
WT    Ku70-/-    Ku80-/-
BM
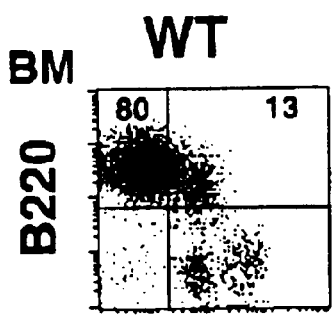 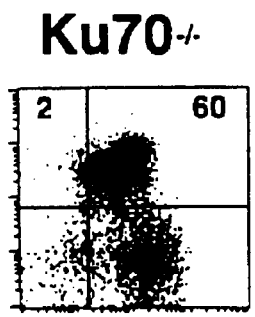 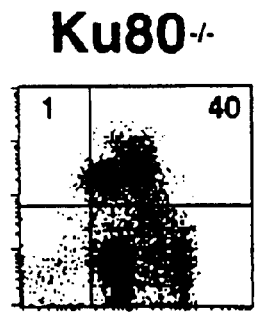
CD43
FIG. 2B-4    FIG. 2B-5    FIG. 2B-6
Spl
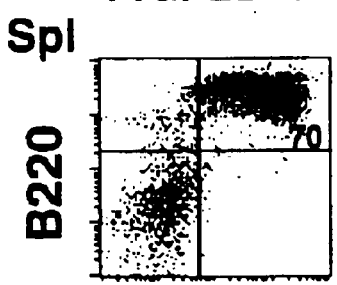 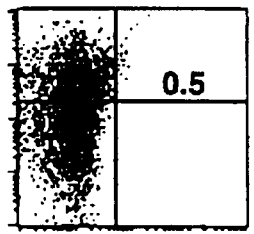 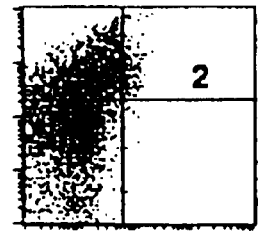
IgM
FIG. 2B-7    FIG. 2B-8    FIG. 2B-9
Thy
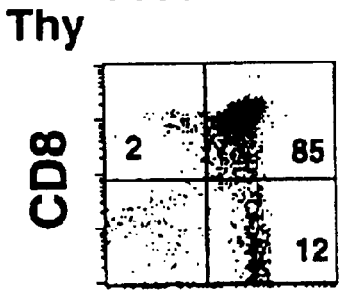 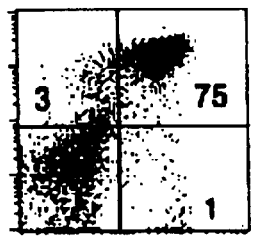 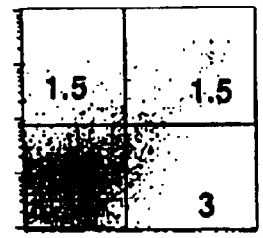
CD4
FIG. 2B-10    FIG. 2B-11    FIG. 2B-12
Spl
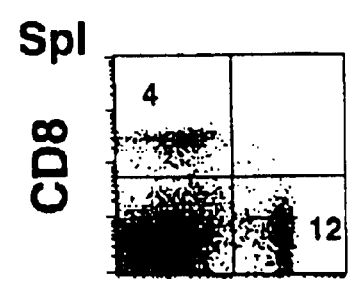 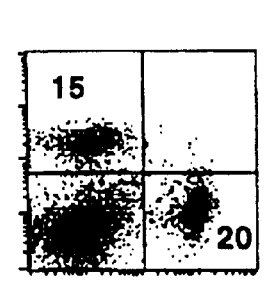 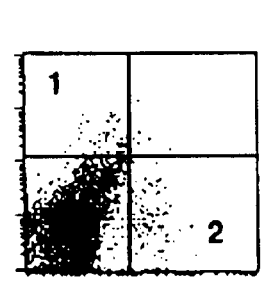
CD4

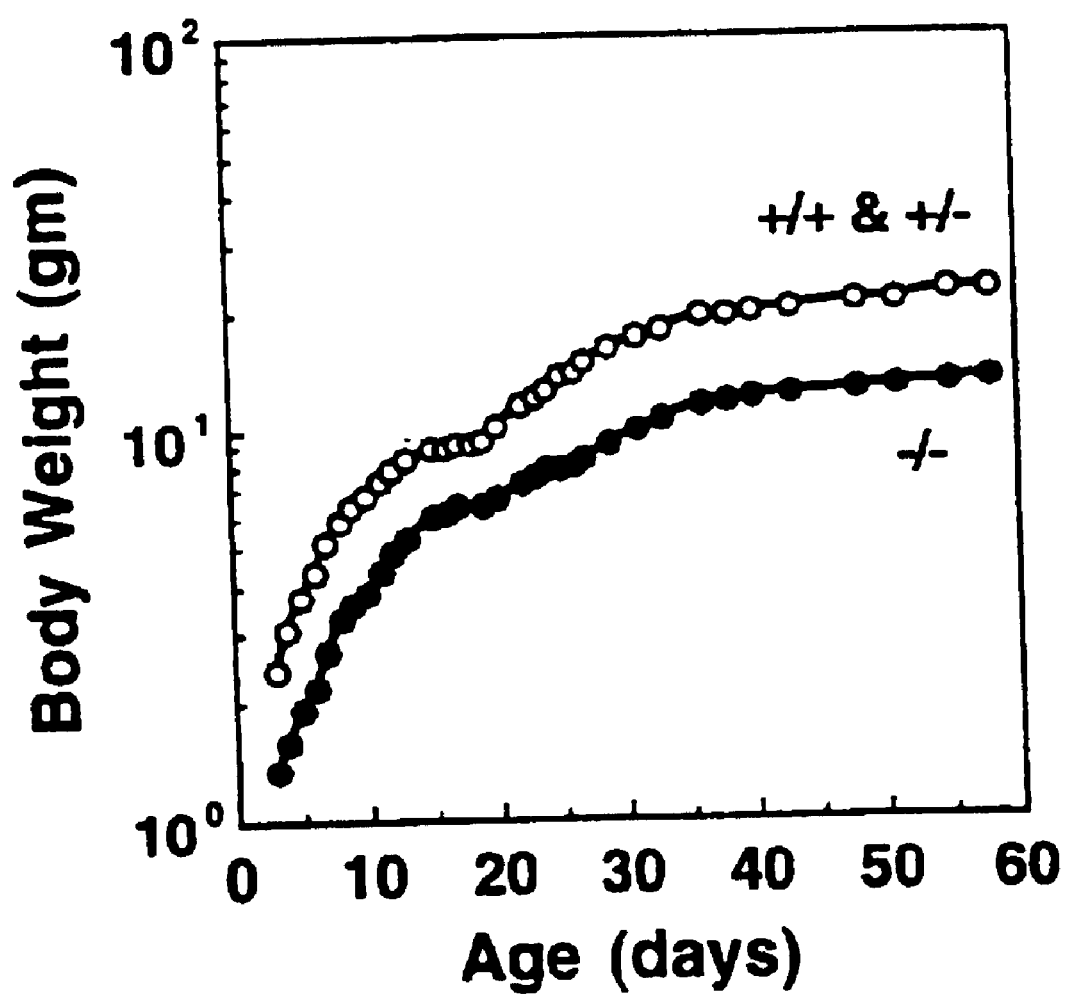

Ku70 +/+     Ku70 -/-

     

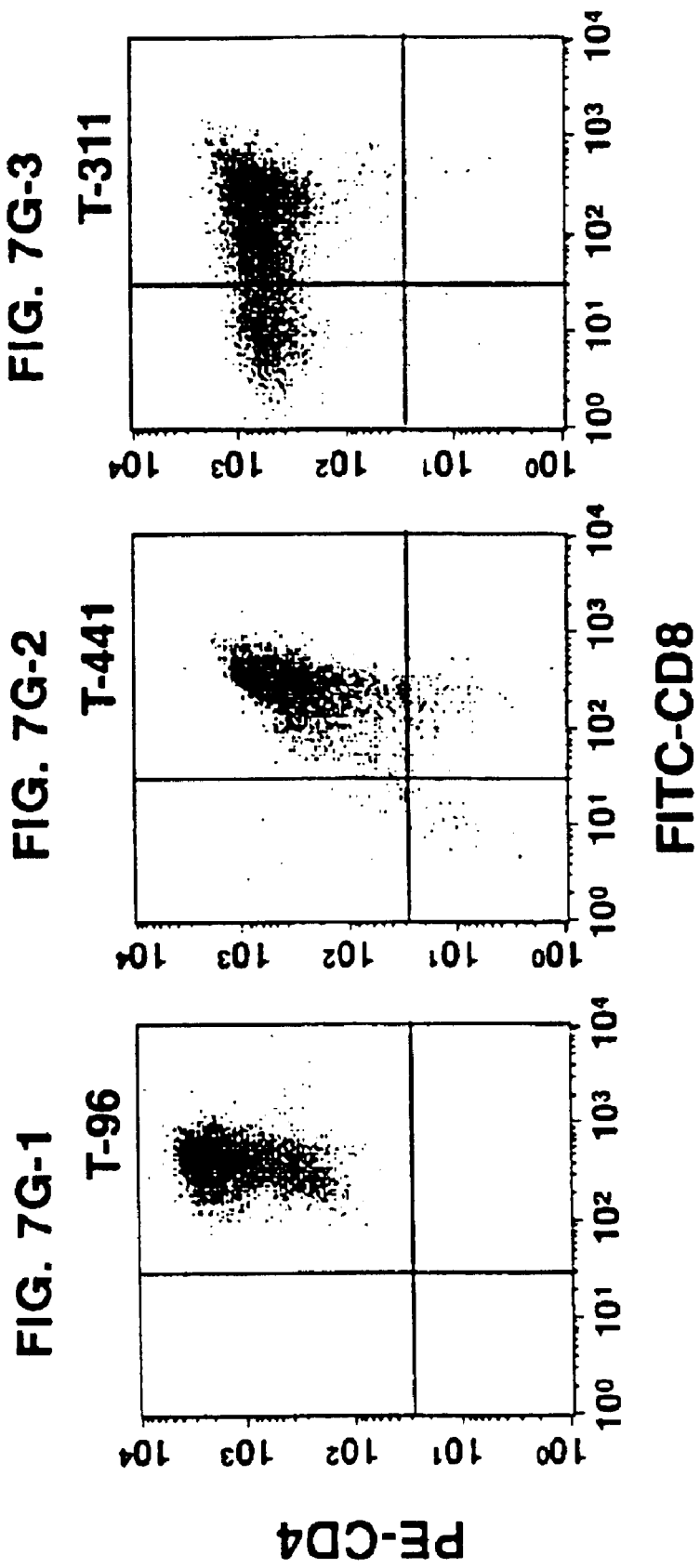

wt (+/+)  70 (+/-)  70 (-/-)

wt (+/+)  70 (-/-)  focus T1  focus C2

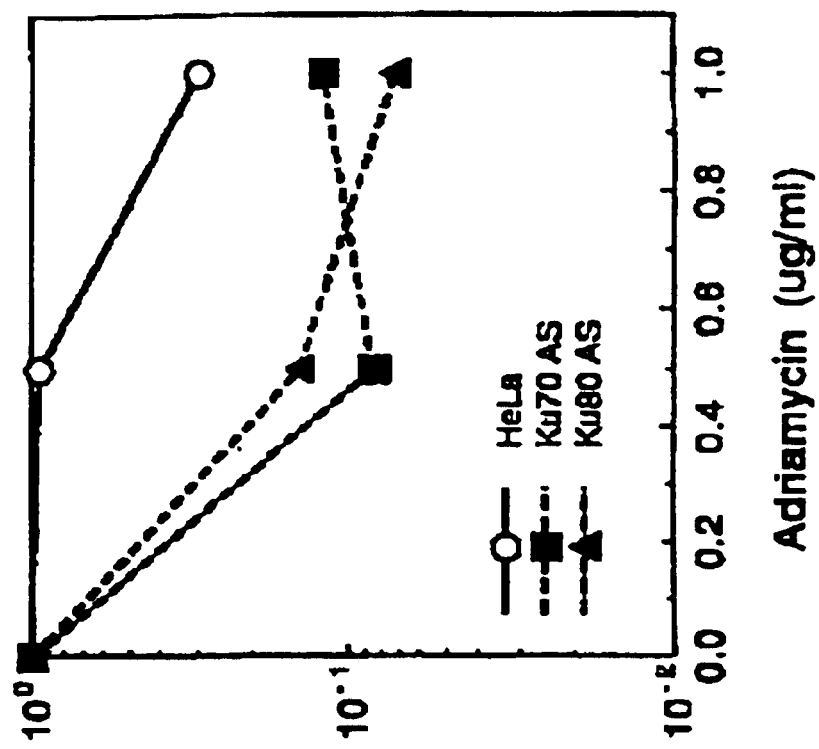
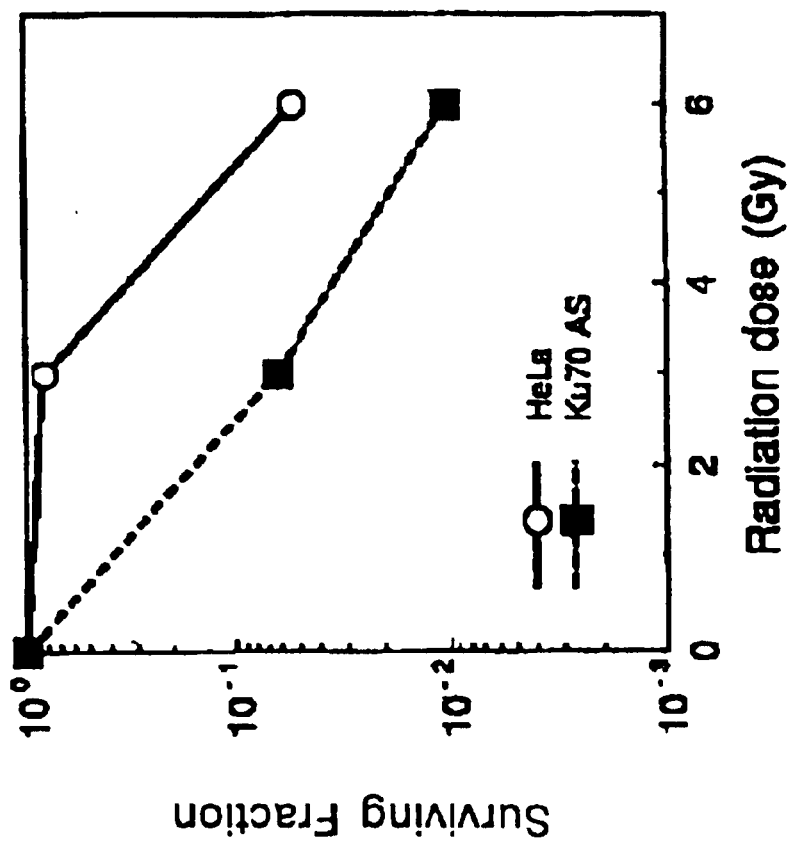

FIG. 14

| V$_\beta$8.1 | P | N | D$_\beta$2.1 | N | P | J$_\beta$2.6 |
|---|---|---|---|---|---|---|
| AGCTGTATATTTCTGTGCCAGCAGTGATG | | | GGGACTGGGGGGC | | | CTCCTATGAACAGTACTTCGGTCCCGGCACCA |
| AGCTGTATATTTCTGTGCCAGCAGTG | | | GGAC | AGT | | TGAACAGTACTTCGGTCCCGGCACCA (2) |
| AGCTGTATATTTCTGTGCCAGC | | CGACA | GG | | | CTCCTATGAACAGTACTTCGGTCCCGGCACCA |
| AGCTGTATATTTCTGTGCCAGC | | CTG | GGGGG | | | CTATGAACAGTACTTCGGTCCCGGCACCA |
| AGCTGTATATTTCTGTGCCAGCAGTG | | | GGGA | | | GAACAGTACTTCGGTCCCGGCACCA |
| AGCTGTATATTTCTGTGCCAGCAGTGA | | | | | | CTCCTATGAACAGTACTTCGGTCCCGGCACCA |

| V$_\beta$8.2 | | | | | | |
|---|---|---|---|---|---|---|
| ATCAGTGTACTTCTGTGCCAGCGGTGATG | | | | | | |
| ATCAGTGTACTTCTGTGCCAGCGGTG | | | C | GGGGGGGC | | TGAACAGTACTTCGGTCCCGGCACCA |
| ATCAGTGTACTTCTGTGCCAGCGG | | GCC | | TT | | GAACAGTACTTCGGTCCCGGCACCA |
| ATCAGTGTACTTCTGTGCCAGCGGTA | | | | | | GTACTTCGGTCACGGCTCCA |
| ATCAGTGTACTTCTGTGCCAGC | | | CG | | | CTCCTATGAACAGTACTTCGGTCCCGGCACCA |
| ATCAGTGTATTTCTGTGCCAGC | | | GG | T | | TGAACAGTACTTCGGTCCCGGCACCA |
| ATCAGTGTACTTCTGTGCCAGC | | CA | GGGA | | AG | CTCCTATGAACAGTACTTCGGTCCCGGCACCA |

| V$_\beta$8.3 | | | | | | |
|---|---|---|---|---|---|---|
| ATCTTTGTACTTCTGTGCCAGCAGTGATG | | | | | | |
| ATCTTTGTACTTCTGTGCCAGCAGTG | CA | | GGGG | | | CCTATGAACAGTACTTCGGTCCCGGCACCA |
| ATCTTTGTACTTCTGTGCCAGCAGC | | | TG | | | TACTTCGGTCCCGGCACCA |
| ATCTTTGTACTTCTGTGCCAGCAGTGAT | | | TCGG | | | CCTATGAACAGTACTTCGGTCCCGGCACCA |
| ATCTTTGTACTTCTGTGCCAGCAGTGAT | | | | | | CCTATGAACAGTACTTCGGTCCCGGCACCA |
| ATCTTTGTACTTCTGTGCCAGCAGTGA | | | | C | | CCTATGAACAGTACTTCGGTCCCGGCACCA |
| ATCTTTGTACTTCTGTGCCAGCAGTGA | | | | | | CCTATGAACAGTACTTCGGTCCCGGCACCA |

USES OF KU70

This application is a divisional of U.S. Ser. No. 09/343,634, filed Jun. 30, 1999 now U.S. Pat. No. 6,399,298, claiming the benefit of U.S. Provisional Application No. 60/091,188, filed Jun. 30, 1998, the contents of which are hereby incorporated by reference.

The invention disclosed herein was made with Government support under NIH Grant Nos. CA-31397 and CA-56909 from the Department of Health and Human Services and the Department of Energy OHER (DC). Accordingly, the U.S. Government has certain rights in this invention.

Within this application, publications are referenced within parentheses. Full citations for these references may be found at the end of each series of experiments. The disclosures of these publications in their entireties are hereby incorporated by reference into this application in order to more fully describe the state of the art to which this invention pertains.

BACKGROUND OF THE INVENTION

Two distinct processes involving DNA double-strand breaks (DSB) have been identified in mammalian cells: the repair of DNA damage induced by ionizing radiation and V(D)J recombination during T- and B-cell development. So far, all mammalian cell mutants defective in DNA DSB repair share the common phenotype of hypersensitivity to radiation, and impaired ability to undergo V(D)J recombination (1–6). Cell fusion studies using DSB repair mutants of human-rodent somatic hybrids have defined four complementation groups: IR4, IR5, IR6, and IR7. Genetic and biochemical analyses have revealed that cells of IRS (e.g., xrs-6) and IR7 (e.g., scid) are defective in components of the DNA-dependent protein kinase (DNA-PK) (2, 7–9). DNA-PK is a serine/threonine kinase comprised of a large catalytic subunit (DNA-PK$_{cs}$) and a DNA-targeting component termed Ku, which itself is a heterodimer of a 70-kDa (Ku70) and a 86-kDa (Ku80) polypeptide (10–12). Recently, DNA-PK$_{cs}$ has been shown to be the gene responsible for the murine scid (severe combined immunodeficiency) defect (13–15); and Ku80 has been identified to be XRCC5 (16–18), the X-ray-repair cross-complementing gene for IR5. Ku80 knockout mice were found to exhibit severe combined immunodeficiency, defective processing of V(D)J recombination intermediates, and growth retardation (19, 20).

Though Ku70 has been designated as XRCC6 (7, 8) and is an important component of the DNA-PK complex, the function of Ku70 in vivo is hitherto unknown. To define the role of Ku70 in DNA repair and V(D)J recombination, we targeted the Ku70 gene in mice. Ku70 homozygotes exhibit proportional dwarfism, a phenotype of Ku80$^{-/-}$, but not of scid mice. Absence of Ku70 confers hypersensitivity to ionizing radiation and deficiency in DNA DSB repair, which are characteristics of both Ku80$^{-/-}$ and scid mice. Surprisingly, in contrast to Ku80$^{-/-}$ and scid mice, in which both T- and B-lymphocyte development are arrested at early stage, lack of Ku70 is compatible with T cell receptor gene recombination and the development of mature CD4$^+$CD8$^-$ and CD4$^-$CD8$^+$ T cells. Our data, for the first time, provide direct evidence supporting that Ku70 plays an essential role in DNA DSB repair, but is not required for TCR gene recombination. These results suggest that distinct but overlapping repair pathways may mediate DSB repair and V(D)J rejoining; furthermore, it suggests the presence of a Ku70-independent rescue pathway in TCR V(D)J recombination.

The distinct phenotype of Ku70$^{-/-}$ mice should make them valuable tools for unraveling the mechanism(s) of DNA repair and recombination.

Ku is a complex of two proteins, Ku70 and Ku80, that functions as a heterodimer to bind DNA double-strand breaks (DSB) and activate DNA-dependent protein kinase (DNA-PK). The role of the Ku70 subunit in DNA DSB repair, hypersensitivity to ionizing radiation and V(D)J recombination was examined in mice that lack Ku70 (Ku70$^{-/-}$). Like Ku80$^{-/-}$ mice, Ku70$^{-/-}$ mice showed a profound deficiency in DNA DSB repair and were proportional dwarfs. Surprisingly, in contrast to Ku80$^{-/-}$ mice, in which both T- and B-lymphocyte development were arrested at early stage, lack of Ku70 was compatible with T cell receptor gene recombination and the development of mature CD4$^+$CD8$^-$ and CD4$^-$CD8$^+$ T cells. Our data shows, for the first time, that Ku70 plays an essential role in DNA DSB repair, but is not required for TCR V(D)J recombination. These results suggest that distinct but overlapping repair pathways may mediate DNA DSB repair and V(D)J recombination.

SUMMARY OF THE INVENTION

This invention provides a method of diagnosing a predisposition to cancer in a subject comprising: (a) obtaining a nucleic acid sample from the subject; and; (b) determining whether one or more of the subject's Ku70 alleles or regulatory regions to those alleles are deleted or different from the wild type so as to reduce or eliminate the subject's expression of polypeptide having tumor suppressor activity.

This invention also provides a method of assessing the severity of cancer in a subject comprising: (a) obtaining a nucleic acid sample from the subject; and (b) determining whether one or more of the subject's Ku70 alleles or regulatory regions to those alleles are deleted or different from the wild type so as to reduce or eliminate the subject's expression of polypeptide having tumor suppressor activity.

This invention also provides a method of assessing the severity of cancer in a subject comprising: determining the subcellular localization of Ku70 in the subject, wherein an abnormal subcellular localization of Ku70 indicates a predisposition to cancer.

In addition, this invention provides the above-described methods, wherein the abnormal subcellular localization of Ku70 comprises increased cytosolic localization of Ku70.

In addition, this invention provides a method of inhibiting the growth of cancer cells, comprising introducing into a cell a Ku70 gene under conditions permitting expression of the gene.

This invention also provides the above-described methods, wherein the cancer is T-cell lymphoma.

In addition, this invention provides the above-described methods, wherein the cell prior to the introduction of the Ku70 gene was characterized as having a mutation at one or more Ku70 alleles or regulatory regions thereto.

In addition, this invention provides the above-described methods, wherein the cell prior to the introduction of the Ku70 gene was characterized as having reduced expression of Ku70.

This invention further provides the above-described methods, wherein the Ku70 gene is incorporated into an expression vector prior to introduction into the cell.

This invention also provides a method of inhibiting the growth of cancer cells, comprising introducing Ku70 into a cell.

In addition, this invention provides the above-described methods, wherein the cancer is T-cell lymphoma.

In addition, this invention provides a transgenic cell, wherein the expression of the Ku70 allele have been altered to increase the susceptibility of the cell to DNA damage.

This invention also provides a transgenic cell, wherein the expression of the Ku70 allele has been altered to increase the susceptibility of the cell to cancerous growth.

This invention also provides a transgenic organism, comprising an organism whose germ line cells has been altered at the Ku70 allele to produce an organism whose offspring have an increased likelihood of developing tumors.

In addition, this invention provides a transgenic organism, comprising an organism whose germ line cells has been altered at the Ku70 allele to produce an organism whose offspring have an increased likelihood of having increased susceptibility to DNA damage.

This invention further provides a method of screening a compound for carcinogenic activity, comprising: (a) contacting cells having reduced expression of Ku70 with the compound; and (b) determining whether the compound results in a malignant transformation phenotype.

This invention also provides a method of screening a compound for ability to restore Ku70 activity to cells having Ku70 defect symptoms resulting from reduced Ku70 activity, comprising: (a) contacting cells having reduced expression of Ku70 with the compound; and (b) determining whether the compound restores, in whole or in part, a normal Ku70 phenotype.

BRIEF DESCRIPTION OF THE FIGURES

FIG. 7 Histological analysis of the spontaneous tumors that developed in Ku70$^{-/-}$ mice. (A & D) Photomicrographs of sections of a thymic lymphoma processed as follows: (A), hematoxylin and eosin staining; (D), positive immunohistochemical surface staining against T-cell surface marker CD3. (B, C, E and F) Photomicrographs of sections of lung tissues showing tumor involvement. (B) and (C), hematoxylin and eosin; (E) and (F), positive immunohistochemical surface staining against T-cell surface marker CD3. B, bronchial lumen; V, blood vessel. (G) Flow cytometric analysis of tumor cells. Cells were labeled with PE-conjugated anti-CD4 and FITC-conjugated anti-CD8 antibodies. Original magnifications: A, C, D and F, 400×; B and E, 100×.

FIG. 13 Effect of (A) radiation, and (B) adriamycin on different cell types. o=HeLa controls cells; ■=HeLa cells expressing antisense Ku70; ▲=HeLa cell expressing antisense Ku80.

FIG. 14 Nucleotide sequences of Vβ8Dβ2.1Jβ2.6 junctions from the thymus of a 4 week old Ku70$^{-/-}$ mouse. Products corresponding to Vβ8.1, Vβ8.2 or Vβ8.3 rearrangement with Jβ2.6 were cloned and sequenced. TCR Vβ8-Jβ2 joints were amplified by PCR (20, 27, 28) as described (see FIG. 3B). PCR cycling conditions were 94° C. for 45", 68° C. for 30", and 72° C. for 30"(30 cycles). The band corresponding to Vβ8-Jβ2.6 was purified, reamplified for 20 cycles and then subcloned into the PCRII vector (Invitrogen). DNA was extracted from individual colonies and sequenced using the universal T7 and M13 reverse primers. Germline sequences are written in bold case, 'N' and 'P' denote nucleotides not present in the germline sequences.

DETAILED DESCRIPTION OF THE INVENTION

Figure 1A:
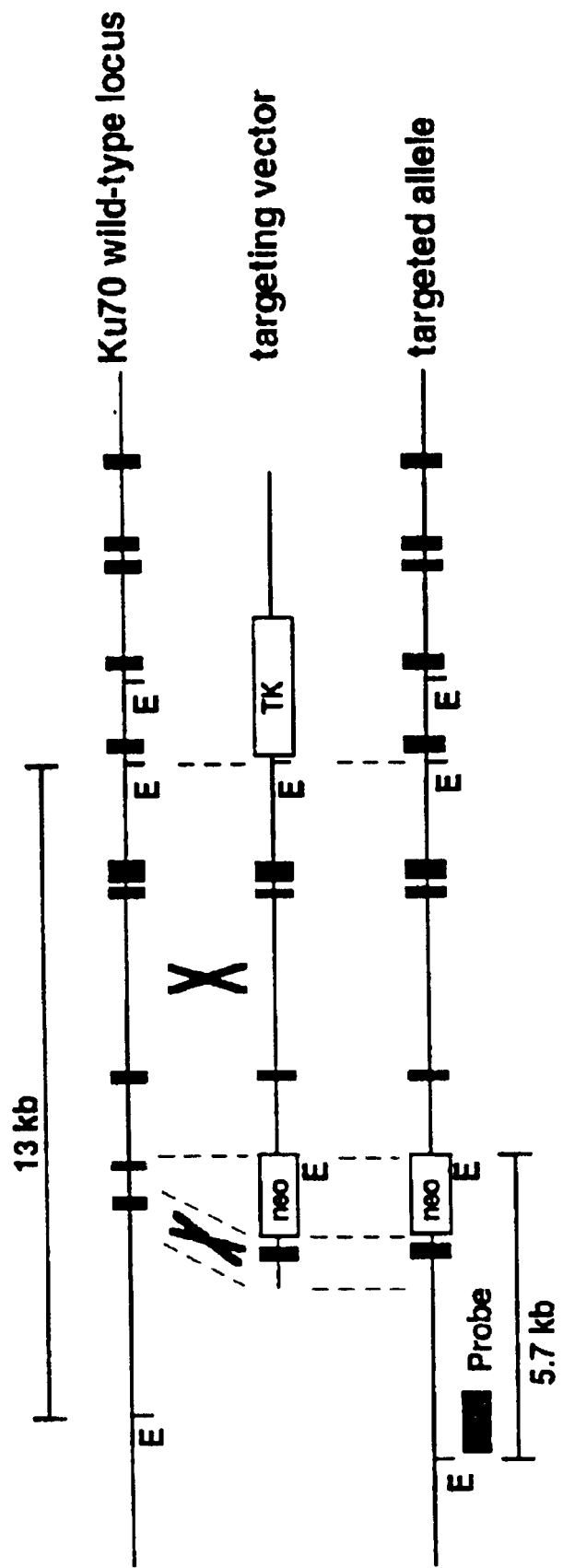
FIG. 1 Inactivation of Ku70 by homologous recombination. (A) Diagrammatic representation of the Ku70 locus (top), the targeting construct (middle), and the targeted allele and hybridization probe (bottom). EcoRI restriction sites used to detect the targeted gene are indicated (21). (B) Southern blot of EcoRI-digested tail DNA from control wild type (WT), heterozygous ($+/-$) and homozygous ($-/-$) Ku70-targeted mice. The wild-type and mutant fragments are 13 and 5.7 kb respectively. (C) Western blot analysis showing that Ku70 protein is not expressed in Ku70$^{-/-}$ cells. Whole-cell lysates prepared from mouse ear fibroblasts (50 $\mu$g) and mouse embryo fibroblasts (100 $\mu$g) were separated by 10% SDS-PAGE, transferred to a nitrocellulose membrane, and probed with polyclonal antibodies against full-length rodent Ku80 (top) and Ku70 (bottom), respectively. (D) Gel mobility shift assay (22) showing the lack of DNA-end binding activity in Ku70$^{-/-}$ cells. Ku-DNA binding complex is indicated by arrow on the right.

This invention provides a method of diagnosing a predisposition to cancer in a subject comprising: (a) obtaining a nucleic acid sample from the subject; and; (b) determining whether one or more of the subject's Ku70 alleles or regulatory regions to those alleles are deleted or different from the wild type so as to reduce or eliminate the subject's expression of polypeptide having tumor suppressor activity.

Nucleic acid samples can be obtained from numerous sources which include, but are not limited to, blood, saliva, tissue, and hair follicles.

Ku70 allele and regulatory element differences from the wild type include, but are not limited to, deletions, additions, substitutions, and chemical modification of Ku70. Chemical modifications of Ku70 and/or its regulatory elements include, but are not limited to, nucleotide phosphorylation, methylation, and/or hydroxylation. Sites of nucleotide differences include, but are not limited to, introns, exons, enhancers, promoters, splice junctions, splice site consensus sequences, RNA-cleavage/polyadenylation sites, cap sites, and other protein binding sites. In an embodiment, protein binding sites are located by "footprinting", wherein a protein shields the nucleic acid from cleavage by restriction enzymes.

Ku70 allele or regulatory differences also include, but are not limited to, sequence changes that alter the relative distance of the Ku70 allele from its regulatory elements. In an embodiment, an insertion increases the distance of Ku70 from an enhancer. In another embodiment, an deletion, increase the proximity of Ku70 to its promoter.

Ku70 regulatory differences further include hypermethylation of regulatory regions. In an embodiment, the promoter to Ku70 is hypermethylated. In another embodiment, the enhancer to Ku70 is hypermethylated.

In an embodiment, hypermethylation is associated with regions of DNA that have reduced activity or no activity. In an embodiment methylation of Ku70 promoter sequences is likely to reduce transcription of Ku70. In an embodiment, methylation of other regions of Ku70, besides the promoter, including the coding region would also be indicative of reduced Ku70 activity. In an embodiment methylation of Ku70 or its regulatory regions occurs at CG pairs. In another embodiment, methylation of Ku70 or its regulatory regions occurs at sites containing a high a frequency of CG pairs.

In an embodiment, methylation is assessed by using restriction endonucleases whose recognition sequences contain CG. For example, HpaII and MspI both recognize CCGG. However, HspII cleaves only unmethylated DNA while MspI cleaves both methylated and unmethylated DNA. Using these two restriction enzymes, one skilled in the art could infer from the size of the restriction fragments the presence of methylation in Ku70 or its regulatory elements.

This invention also provides the above-described method, wherein the cancer is T-cell lymphoma.

This invention further provides the above-described methods, wherein the cancer is B-cell lymphoma.

This invention also provides the above-described methods, wherein the cancer is neuroblastoma.

In addition, this invention provides the above-described methods, wherein the regulatory region is a promoter.

This invention further provides the above-described methods, wherein the determining of step b comprises generating a polypeptide encoded by one or more of the subject's Ku70 alleles and comparing the resulting polypeptide to a wild type Ku70 polypeptide.

In an embodiment, comparing a polypeptide to Ku70 can be done by comparing the polypeptide with wild type Ku70 for Ku70-type activity. Significant differences may result in Ku70 defect symptoms, which include, but are not limited to, impaired DNA double-strand break repair, impaired V(D)J recombination, proportional dwarfism, increased sister chromatid exchange, and hypersensitivity to ionizing radiation. Given Ku70's role DNA double strand break repair other functional assays would be readily apparant to one skilled in the art.

In another embodiment, comparing a polypeptide to Ku70 can be done by comparing the polypeptide sequences. One skilled in the art would be able recognize sequence differences and chemical modifications that would influence the polypeptides activity. For example, substitutions that change the charge of amino acids in important functional domains are likely to influence Ku70 activity.

In a different embodiment, comparing a polypeptide to Ku70 can be done by testing the polypeptides for immunoreactivity. The ability to generate and react with antibodies is indicative of the structural properties of the polypeptide. For example, a mutation that significantly changes the functional properties of the polypeptide may also alter the polypeptides structural shape (i.e. conformation) in a manner that may mask or unmask various epitopes. Such structural changes may be detected by antibodies that recognize epitopes in regions influence by the structural changes.

This invention also provides the above-described methods, wherein the nucleic acid sample is obtained from the subject's blood.

This invention further provides a method of diagnosing a predisposition to cancer in a subject comprising: determining the level of Ku70 expression in the subject.

In addition, this invention provides the above-described methods, wherein the cancer is T-cell lymphoma.

This invention also provides the above-described methods, wherein the cancer is B-cell lymphoma.

In addition, this invention provides the above-described methods, wherein the cancer is neuroblastoma.

This invention provides the above-described methods, wherein the level of Ku70 expression is determined based upon the level of Ku70 mRNA in the subject.

This invention also provides the above-described methods, wherein the level of Ku70 expression is determined based upon the level of Ku70 polypeptide in the subject.

This invention further provides the above-described methods, wherein zero or reduced Ku70 expression indicates a predisposition to cancer.

In addition, this invention provides a method of diagnosing a predisposition to cancer in a subject comprising: determining the subcellular localization of Ku70 in the subject, wherein an abnormal subcellular localization of Ku70 indicates a predisposition to cancer.

This invention also provides the above-described methods, wherein the abnormal subcellular localization of Ku70 comprises increased cytosolic localization of Ku70.

This invention further provides the above-described methods, wherein the abnormal subcellular localization of Ku70 comprises decreased nuclear localization of Ku70.

This invention also provides a method of assessing the severity of cancer in a subject comprising: (a) obtaining a nucleic acid sample from the subject; and (b) determining whether one or more of the subject's Ku70 alleles or regulatory regions to those alleles are deleted or different from the wild type so as to reduce or eliminate the subject's expression of polypeptide having tumor suppressor activity.

In addition, this invention provides the above-described methods, wherein the cancer is T-cell lymphoma.

This invention further provides the above-described methods, wherein the cancer is B-cell lymphoma.

This invention further provides the above-described methods, wherein the cancer is neuroblastoma.

This invention also provides a method of assessing the severity of cancer in a subject comprising: determining the subcellular localization of Ku70 in the subject, wherein an abnormal subcellular localization of Ku70 indicates a predisposition to cancer.

In addition, this invention provides the above-described methods, wherein the abnormal subcellular localization of Ku70 comprises increased cytosolic localization of Ku70.

This invention also provides the above-described methods, wherein the abnormal subcellular localization of Ku70 comprises decreased nuclear localization of Ku70.

Further, this invention provides a method of inhibiting the growth of cancer cells, comprising introducing into a cell a Ku70 gene under conditions permitting expression of the gene.

In addition, this invention provides a method of inhibiting cancer, comprising introducing into a cell a Ku70 gene under conditions permitting expression of the gene.

This invention also provides the above-described methods, wherein the cancer is T-cell lymphoma.

As used herein, inhibiting T-cell lymphoma includes, reducing the likelihood of or preventing the occurrence of T-cell lymphoma in a subject who does not have T-cell lymphoma. Inhibiting T-cell lymphoma further includes, reducing or eliminating the occurrence of T-cell lymphoma in a subject who does have T-cell lymphoma.

This invention further provides a method of inhibiting the growth of cancer cells, comprising introducing into a cell a Ku70 gene under conditions permitting expression of the gene.

This invention provides the above-described methods, wherein the cancer is B-cell lymphoma.

This invention further provides the above-described methods, wherein the cancer is neuroblastoma.

In addition, this invention provides the above-described methods, wherein the cell prior to the introduction of the Ku70 gene was characterized as having a mutation at one or more Ku70 alleles or regulatory regions thereto.

This invention also provides the above-described methods, wherein the mutation is a frameshift mutation.

This invention provides the above-described methods, wherein the mutation is a point mutation.

In addition, this invention provides the above-described methods, wherein the cell prior to the introduction of the Ku70 gene was characterized as having reduced expression of Ku70.

This invention further provides the above-described methods, wherein the Ku70 gene is incorporated into an expression vector prior to introduction into the cell.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

In an embodiment, inducible promoters may be fused with the coding region of the DNA to provide an experimental means to regulate expression. Alternatively or in addition, tissue specific regulatory elements may be fused with the coding region to permit tissue-specific expression.

This invention also provides a method of inhibiting the growth of cancer cells, comprising introducing Ku70 into a cell.

This invention also provides a method of inhibiting cancer, comprising introducing Ku70 into a cell.

In addition, this invention provides the above-described methods, wherein the cancer is T-cell lymphoma.

This invention also provides the above-described methods, wherein the cancer is B-cell lymphoma.

This invention further provides the above-described methods, wherein the cancer is neuroblastoma.

In addition, this invention provides a transgenic cell, wherein the expression of the Ku70 allele has been altered to increase the susceptibility of the cell to DNA damage.

This invention also provides a transgenic cell, wherein the expression of the Ku70 allele has been altered to increase the susceptibility of the cell to cancerous growth.

This invention also provides a transgenic organism, comprising an organism whose germ line cells has been altered at the Ku70 allele to produce an organism whose offspring have an increased likelihood of developing tumors.

Germ line cells include, but are not limited to, spermatogonium, primary spermatocytes, secondary spermatocytes, spermatids, sperm cells, oogonium, primary oocytes, second oocytes, and egg cells.

Methods to introduce a nucleic acid into cells have been well known in the art. Naked nucleic acid may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, calcium phosphate coprecipitation, mechanical or electrical means (i.e. electroporation).

Transgenic organisms may be created by a variety of techniques. One such technique is introducing normal or mutant genes into fertilized embryos. In an embodiment, the gene is cloned and then microinjected into the pronuclei of a fertilized egg.

One example of producing a transgenic animal is as follows: female mice are mated, and the resulting fertilized eggs are dissected out of their oviducts. The eggs are stored in an appropriate medium such as M2 medium. DNA or cDNA encoding a Ku70 is purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. Microinjection is not the only method for inserting DNA into the egg cell, and is used here only for exemplary purposes.

Another technique for generating a transgenic organism is introducing the DNA into embryonic stem cells and then injecting the transfected stem cells into embryos where they may become incorporated into the developing embryo. This technique has the advantage of creating the opportunity for screening and selecting particular transfected stem cells prior to their incorporation into the embryo. In an embodiment, antibiotic resistance may be used to select for stem cells that have taken up the DNA of interest. In another embodiment, PCR may be used to screen for stems cell that have incorporated only one copy of the transgene. In another embodiment, PCR and/or sequencing can be used to screen for stem cells that have incorporated the transgene through homologous recombination.

When DNA is introduced into a cell, the incorporation of the DNA into the cell's genome is dependent on recombination events. Recombination is of two types: heterologous recombination, wherein the DNA recombines into an unrelated sequence; and homologous recombination, wherein the DNA recombines into an identical or allelic variant of the sequence in the genome. Homologous recombination is common in bacteria, yeast, and certain viruses, but is rare in mammalian cells. Using homologous recombination, it is possible to create organisms in which the function of the native gene has been "knocked out." By introducing the DNA into embryonic stem cells, it is possible to select or screen for specific cell types for introduction into embryos. For example, PCR may be used to screen for homologous recombination events in embryonic stem cells. By selecting for such events and introducing the stem cells into mouse embyros, "knockout mice", may be created in which specific genes have been replaced by different nucleic acid sequences that do not encode the native protein.

Prior to its incorporation into the cellular DNA, the DNA fragments to be introduced often become ligated end-to-end by enzymes in the cell, thus forming long tandem arrays. Because of ligation, transgenic organisms may contain several copies of the transgene.

Chimeric transgenic organisms may result from the above-described techniques. For example, the embryonic stems cells introduced into a blastocyst may codevelop with the other embryonic cells native to the blastocyst. The resulting organism may have somatic cells that differ in their genetic content. In an example, a transgenic rabbit may have different colored patches of fur resulting from a coat color transgene. If the germ line cells of a transgenic organism have incorporated the transgene, then the offspring of the transgenic organism may also incorporate the transgene. In an embodiment, chimeric transgenic organisms whose germ line cells have incorporated the transgene may be bred together to produce transgenic organisms that have the transgene throughout their cells.

In addition, this invention provides a transgenic organism, comprising an organism whose germ line cells has been altered at the Ku70 allele to produce an organism whose offspring have an increased likelihood of having increased susceptibility to DNA damage.

This invention provides the above-described transgenic organisms, wherein the somatic cells have been altered to reduce or eliminate expression of Ku70.

This invention also provides the above-described transgenic organisms, wherein the somatic cells have been alterred to reduce or eliminate expression of Ku70.

This invention also provides the above-described transgenic organisms, wherein the organism is a mouse.

This invention provides the above-described transgenic organisms, wherein the organism is a mouse.

This invention further provides a method of screening a compound for carcinogenic activity, comprising: (a) contacting cells having reduced expression of Ku70 with the compound; and (b) determining whether the compound results in a malignant transformation phenotype.

A malignant transformation phenotype includes but is not limited to metastasis and/or anchorage independent growth.

This invention also provides the above-described methods, wherein the cell is a fibroblast.

In addition, this invention provides the above-described methods, wherein the malignant transformation phenotype comprises anchorage independent growth.

This invention provides a method of screening a compound for DNA damaging activity, comprising: (a) contacting cells having reduced expression of Ku70 with the compound; and (b) determining whether the compound results in DNA damage.

This invention also provides the above-described methods, wherein the DNA damage is determined by measuring a reduction in cell survival.

In addition, this invention provides the above-described methods, wherein the DNA damage comprises one or more double strand breaks.

This invention also provides a method of screening a compound for ability to restore Ku70 activity to cells having Ku70 defect symptoms resulting from reduced Ku70 activity, comprising: (a) contacting cells having reduced expression of Ku70 with the compound; and (b) determining whether the compound restores, in whole or in part, a normal Ku70 phenotype.

This invention will be better understood from the examples which follow. However, one skilled in the art will readily appreciate that the specific methods and results discussed are merely illustrative of the invention as described more fully in the claims which follow thereafter.

Experimental Details
First Series of Experiments
Material and Methods
Target Disruption of Ku70 and Generation of Ku70$^{-/-}$ Mice Mouse genomic Ku7o gene was isolated from a sCos-I cosmid library constructed from a mouse strain 129 embryonic stem cell lines (21). The replacement vector was constructed using a 1.5 kb 5'-fragment which contains the promoter locus with four GC-box and exon 1, and a 8 kb EcoRV-EcoRI fragment extending from intron 2 to intron 5 as indicated in FIG. 1a. Homologous replacement results in a deletion of 336-bp exon 2 including the translational initiation codon.

The targeting vector was linearized with NotI and transfected into CJ7 embryonic stem (ES) cells by electroporation using a Bio-Rad Gene Pulser. Three hundred ES cell clones were screened, and 5 clones carrying the mutation in Ku70 were identified by Southern blotting. Positive ES clones were injected separately into C57BL/6 blastocysts to generate chimeric mice. One clone was successfully transmitted through the germline after chimeras were crossed with C57 BL/6 females. Homozygous Ku70$^{-/-}$ mice were generated by crossing Ku70$^{+/-}$ heterozygotes.

The genotype of the mice was first determined by tail PCR analysis which distinguishes endogenous from the targeted Ku70 allele, and subsequently confirmed by Southern blot analysis. The PCR reaction contained 1 $\mu$g genomic DNA; 0.6 $\mu$M (each) of primers HO-2: GGGCCAGCTCATTCCTCCACTCATG, HO-3: CCTA-CAGTGTACCCGGACCTATGCC and HO-4: CGGAACAGGACTG-GTGGTTGAGCC; 0.2 mM (each) DNTP; 1.5 mM MgCl$_2$ and 2.5 U of Taq polymerase. Cycling conditions were 94° C. for 1 min, 64° C. for 1 min, 72° C. for 1 min (30 cycles), followed by an extension at 72° C. for 10 min. Primers HO-2 and HO-4 give a product of the targeted allele that is ~380 bp; primers HO-3 and HO-4 yield a wild type product of 407 bp.

Western Blot Analysis and Gel Mobility Shift Assay

To confirm that the disruption of Ku70 produces a null mutation, Ku70 protein expression was measured by Western blotting using polyclonal antisera against intact mouse Ku70. The lack of Ku70 was also verified by a Ku-DNA-end binding assay (gel mobility shift analysis). Cell extracts were prepared and gel mobility shift assays were performed as described (22). Equal amounts of cellular protein (50 $\mu$g) from Ku70$^{+/+}$(WT), Ku70$^{+/-}$, and Ku70$^{-/-}$ mouse embryo fibroblasts were incubated with a $^{32}$P-labeled double-stranded oligonucleotide, 5'-GGGCCAAGAATCTTCCAGCAGTTTCGGG-3'. The protein-bound and free oligonucleotides were electrophoretically separated on a 4.5% native polyacrylamide gel. Gel slabs are dried and autoradiographed with Kodak X-Omat film.

Immunohistochemistry

To determine the pathological changes, histological sections of various organs of Ku70$^{-/-}$, Ku80$^{-/-}$ and wild type littermate mice were prepared and examined as previously described (23). Lymph nodes, spleens and thymuses from 4- to 5-week-old mice were fixed in 10% buffered formalin and embedded in paraffin, or embedded in OCT compound (Miles Laboratories) and frozen in liquid nitrogen at −70° C. Sections (5 $\mu$m) were stained with hematoxylin and eosin, and representative samples were selected for immunohistochemical analysis. Immunophenotyping was performed using an avidin-biotin immunoperoxidase technique (24). Primary antibodies included anti-CD3 (purified rabbit serum, 1:1000, Dako), anti-B220 (rat monoclonal, 1:1000, Pharmingen) anti-CD19 (rat monoclonal, 1:1000, Pharmingen), and were incubated overnight at 4° C. Samples were subsequently incubated with biotinylated secondary antibodies (Vector Laboratories) for 30 min (goat anti-rabbit, 1:100; rabbit anti-rat, 1:100), and then with avidin-biotin peroxidase (1:25 dilution, Vector Laboratories) for 30 min. Diaminobenzadine was used as the chromogen and hematoxylin as the counter stain. Wild type lymphoid organs including thymus, spleen and lymph nodes from different mice were used for titration of the antibodies and positive controls. Anti-CD3 and anti-CD19 antibodies were tested in both frozen and paraffin sections of wild-type lymphoid organs and showed the expected specific patterns of staining. For negative controls, primary antibodies were substituted with class-matched but unrelated antibodies at the same final working dilutions.

Cell Preparation and Flow Cytometric Analysis

For flow cytometry, single cell suspensions from lymphoid organs of 4- to 6-week-old mutant and littermate control mice were prepared for staining as described previously (19) and analyzed on a Becton Dickinson FACs Scan with Cell Quest software. Cells were stained with combinations of phycoerythrin-(PE) labeled anti-CD4, and fluorescein (FITC)-labeled anti-CD8, or PE labeled anti-B220, and FITC-labeled anti-CD43, or FITC anti-$\mu$ and PE anti-B220 (Pharmingen), as needed. Bone marrow cells were harvested from femurs by syringe lavage, and cells from thymus and spleen were prepared by homogenization. Cells were collected and washed in PBS plus 5% FCS and counted using a hemacytometer. Samples from individual mice were analyzed separately. Dead cells were gated out by forward and side scatter properties. Experiments were performed at least three times and yielded consistent results.

DNA Preparation and Analysis of V(D)J Recombination Products

To determine whether a null mutation in Ku70 affects the recombination of antigen-receptor genes in T and B lymphocytes in vivo, we measured the immunoglobulin and T-cell antigen receptor (TCR) rearrangements by PCR. DNA from bone marrow was amplified with primers specific to immunoglobulin D-J$_H$ and V-DJ$_H$ rearrangements, and DNA from thymus was amplified with primers that detect V-DJ$_\beta$ and D$_\delta$-J$_\delta$-rearrangement (20, 25–28). Oligonucleotides for probes and PCR primers specific to TCR V$\beta$-J$\beta$ rearrangements and immunoglobulin D-J$_H$ and V$_H$-DJ rearrangements are as follows. For TCRβ8-Jβ2 rearrangements (28): Vβ8.1: 5'-GAGGAAAGGT-GACATTGAGC-3', Jβ2.6: 5'-GCCTGGTGCCGGGACCGAAGTA-3', Vβ8 probe: 5'-GGGCTG AGGCTG ATCCATTA-3'. For D$_{\delta 2}$-J$_{\delta 1}$ rearrangement (20, 27): DR6: 5'-TGGCTTGACATGCAGAAAACACCTG-3', DR53: 5'-TGAATTCCACAG-TCACTTGGCTTC-3', and DR2 probe: 5'-GACACGTGATACAAAGCCCAGGGAA-3'. For immunoglobulin D-J$_H$ and V-DJ$_H$ rearrangements (26): 5'D: 5'-GTCAAGGGATCTACTACTGTG-3', V7183: 5'-GAGAGAATTCAGAGACAATC-CCAAGAACACCCTG-3', VJ558L: 5'-GAGAGAATTCTCCTCCAGCACAG-CCTACATG-3', J2: 5'-GAGAGAATTCGGCTCCCAATGACCCTTTCTG-3', 5'IVS: 5'-GTAAGAATGGCCTCTCCAGGT-3', 3'-IVS: 5'-GACTCAATCACTAAGACA-GCT-3', and probe: a 6 kb EcoR I fragment covering the J region of mouse IgM.

Cell Survival Determination 8- to 10-week-old Ku70$^{-/-}$ and Ku80$^{-/-}$ mice and wild type littermates were used for our studies. Bone marrow cell suspensions were prepared by flushing the femur with MEM supplemented with 15% fetal calf serum (FCS). The cell suspension was then counted using a hemacytometer and centrifuged at 1000 rpm for 12 min. The resulting pellet was resuspended and diluted to approximately $1 \times 10^6$ cells/ml in MEM plus 15% FCS for further experiments.

To measure the survival of granulocyte-macrophage progenitors, the method of Van Zant et al. (29) was used with minor modifications (30). Briefly, α-MEM contained 30% heat-inactivated FCS and 1% bovine serum albumin; in addition, 0.5 ng/ml GM-CSF (R & D Systems) was used as a source of colony-stimulating factor. One day before each experiment, 2.0 ml of the above media containing 0.5% noble agar (DIFCO Laboratories) was added to individual 60-mm petri dishes. Immediately after radiation exposure, cells were diluted in 2 ml of the above media with 0.3% noble agar and poured over the prepared dishes with 0.5% noble agar underlayer. The cells were then incubated at 37° C. with 5% $CO_2$ and 95 to 98% humidity. The colonies were counted on Day 8 with a dissecting microscope. Macrophage and granulocyte colonies were counted separately and then summed together for survival calculations of granulocyte-macrophage progenitors (CFU-GM). Only colonies containing 50 or more cells were scored. The colony forming efficiency of CFU-GMs was 60 to $100/10^5$ nucleated cells for untreated controls. Surviving fraction was defined as the cloning efficiency of irradiated marrow cells relative to that of untreated controls. All experiments were performed at least twice and yielded consistent results.

Asymmetric Field Inversion Gel Electrophoresis

To determine the rate and extent of DNA DSB repair in Ku-deficient cells after exposure to ionizing radiation, primary embryo fibroblasts derived from $Ku70^{-/-}$, $Ku80^{-/-}$ and wild type littermate mice were used. Mouse embryo fibroblasts from 13.5-day embryos growing in replicate cultures for 3 days in the presence of 0.01 $\mu Ci/ml$ $^{14}C$-thymidine (NEN) and 2.5 $\mu M$ cold thymidine were exposed to 40 Gy of X-rays and returned to 37° C. At various times thereafter, one dish was removed and trypsinized on ice; single cell suspensions were made and embedded in an agarose plug at a final concentration of $3 \times 10^6$ cells/ml. AFIGE (Asymmetric Field Inversion Gel Electrophoresis) was carried out in 0.5% Seakem agarose (FMC, cast in the presence of 0.5 $\mu g/ml$ ethidium bromide) in 0.5× TBE (45 mM Tris, pH 8.2, 45 mM boric acid, 1 mM EDTA) at 10° C. for 40 h, by applying cycles of 1.25 V/cm for 900 sec in the direction of DNA migration, and 5.0 V/cm for 75 sec in the reverse direction as described (31). Quantification and analysis for DNA DSB present were carried out in a PhosphorImager (Molecular Dynamics). Levels of DNA double-strand breaks (DSB) were quantified by calculating the FAR (fraction of activity released from the well into the lane) in irradiated and unirradiated samples, which equals the ratio of the radioactivity signal in the lane versus that of the entire sample (well plus lane).

Experimental Results

Targeted Disruption of Ku70 Gene

Figure 1B:
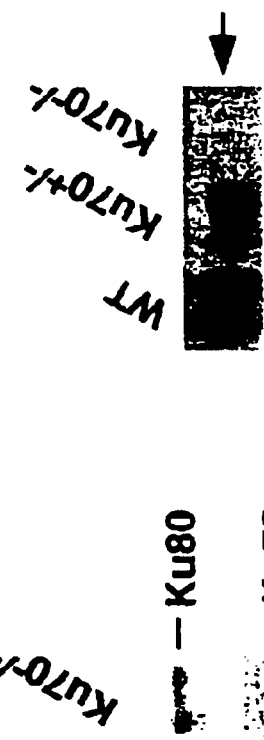

To study the role of Ku70 in vivo, we generated mice containing a germline disruption of the Ku70 gene. Murine genomic Ku70 gene was isolated and a targeting vector was constructed (FIG. 1a). Homologous replacement results in a deletion of 336-bp exon 2 including the translational imitation codon. Two targeted ES clones carrying the mutation in Ku70 were injected into C57BL/6 blastocysts to generate chimeric mice. One clone was successfully transmitted through the germline after chimeras were crossed with C57BL/6 females. No obvious defects were observed in $Ku70^{+/-}$ heterozygotes, and these $Ku70^{+/-}$ mice were subsequently used to generate $Ku70^{-/-}$ mice (FIG. 1b). 25% of the offspring born from $Ku70^{+/-} \times Ku70^{+/-}$ crosses were $Ku70^{-/-}$. Adult $Ku70^{-/-}$ mice are fertile, but give reduced litter size (2 to 4 pups) as compared to the $Ku70^{+/-}$ or $Ku70^{+/+}$ mice (about 8 pups).

Figure 1C:
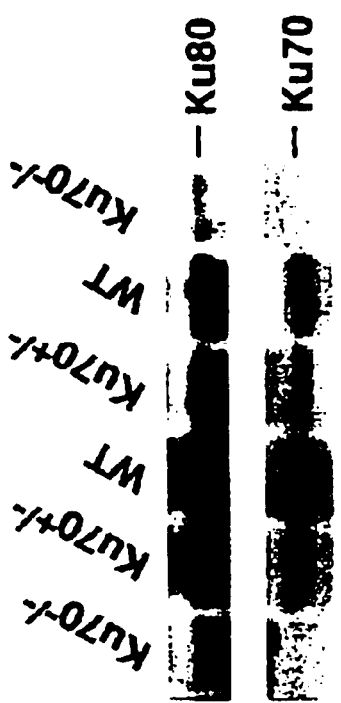
Figure 1D:
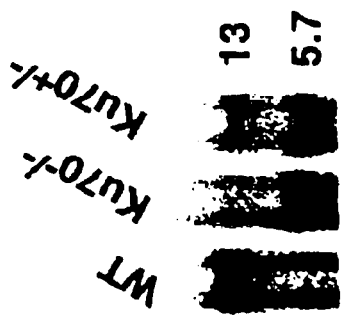

To confirm that the disruption produced a null mutation, Ku70 protein expression was analyzed by both Western blotting (FIG. 1C) and a DNA end binding assay (FIG. 1D). Ku70 immunoreactivity was undetectable (FIG. 1C), and there was no Ku DNA-end binding activity in $Ku70^{-/-}$ fibroblasts (FIG. 1D). The Ku80 subunit of the Ku heterodimer was found, but at much reduced levels (FIG. 1C), suggesting that the stability of Ku80 is compromised by the absence of Ku70. These observations are consistent with the finding that the level of Ku70 was significantly reduced in $Ku80^{-/-}$ fibroblasts and $Ku80^{-/-}$ ES cells (19). Taken together, these data suggest that the stability of either component of Ku is compromised by the absence of the other.

Newborn $Ku70^{-/-}$ mice were 40–60% smaller than their $Ku70^{+/-}$ and $Ku70^{+/+}$ littermates. During a 5-month observation period, $Ku70^{-/-}$ mice grew and maintained body weight at 40–60% of controls. Thus $Ku70^{-/-}$ mice, like $Ku80^{-/-}$ mice are proportional dwarfs (19).

Figures 1, 2A:
Figures 2, 2A:
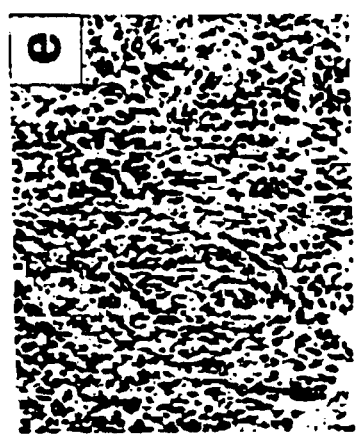
FIG. 2 Development of B lymphocyte, but not T lymphocyte, is blocked at an early stage in Ku70$^{-/-}$ mice. (A) Histology of thymus (Thy), lymph nodes (LN) and spleens (Spl) from wild type control mice, Ku70$^{-/-}$ mice, and Ku80$^{-/-}$ mice (23). Cortex (C) and medulla (M) are indicated. W, white pulp; R, red pulp; GC, germinal center. Panels a to i, tissue sections were stained with haematoxylin and eosin (HE); panels j to l, tissue sections were stained with anti-CD3 (CD3); and panels m to o, tissues were stained with anti-CD19 (CD19). Anti-CD3 and anti-CD19 antibodies were tested in both frozen and paraffin sections of wild-type lymphoid organs and showed the expected specific patterns of staining. (B) Flow cytometric analysis of thymocytes (Thy) bone marrow (BM) and spleen (Spl) cells from Ku70$^{-/-}$ mice, Ku70$^{+/+}$ littermates, and Ku80$^{-/-}$ mice. CD4, anti-CD4 monoclonal antibody; CD8, anti-CD8 monoclonal antibody; B220, anti-B220 monoclonal antibody; CD43, anti-CD43 monoclonal antibody; IgM, anti-Ig$\mu$-heavy-chain monoclonal antibody. The data were gated for live lymphoid cells based on forward and side scatter properties; 10,000–20,000 cells were analyzed per sample. (C) Analysis of TCRβ chain expression in Ku70$^{-/-}$ mice. Thymocytes and spleen cells were obtained from Ku70$^{-/-}$, Ku80$^{-/-}$, and wild type littermates and analyzed for expression of CD4, CD8 and TCRβ by 3-color flow cytometry. The TCRβ expression of both CD4+ and CD8+ single-positive T cells were shown.
Figures 2, 2A, 3:
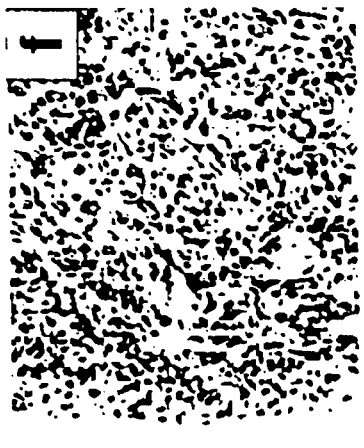
FIG. 3 T-cell antigen receptor and immunoglobulin gene rearrangement in Ku70$^{-/-}$ mice. (A) Recombination of V558L, V7183 to DJ$_H$, and D$_H$ to J$_H$ gene segments (26). 100 ng DNA was used for Ku70$^{-/-}$(lanes 7 and 8), Ku80$^{-/-}$ (lanes 1, 2, and 3), and SCID mice (lanes 4, 5, and 6), and 1, 10 and 100 ng for WT mice (lanes 9–11). For IVS controls, DNA was diluted 100-fold before PCR. (B) PCR analysis of TCR gene rearrangements. Thymus DNA was assayed for recombination of Vβ8-Jβ2 and Dδ2 to Jδ1 rearrangements (20, 27, 28). 100 ng DNA was used for Ku70$^{-/-}$(lanes 2 and 7), Ku80$^{-/-}$(lane 1), and Ku70$^{-/-}$ mice (lane 7) and 1, 10 and 100 ng for WT mice (lanes 4–6). Controls include a 1-kb germline interval amplified in the Dδ2 to Jδ1 intervening region (germline), and a non-recombining segment of the Ig locus between J$_H$ and C$_H$1. The same thymus DNA samples were examined for Vβ8-Jβ2 and Dδ2 to Jδ1 recombination. Abbreviations: DJ$_H$, $_H$D to $_H$J rearrangements; V7183J$_H$ and V558LJ$_H$, V7183 and V558L to DJ$_H$ rearrangements (26); Vβ8Jβ2.1 to Vβ8-Jβ2.6, Vβ8 to DJβ2 rearrangements (28); germline, unrecombined DNA from the Dδ2 to Jδ1 interval; Dδ2Jδ1, Dδ2 to Jδ1 rearrangements (20, 27); IVS, non-recombining segment of the Ig locus between J$_H$ and C$_H$1 (26). Multiple lanes underneath each genotype label (Ku70$^{-/-}$, Ku80$^{-/-}$, and SCID) represent different individual animals.
Figures 2, 2A, 3, 4:
FIG. 4 Disruption of Ku70 confers radiation hypersensitivity and a deficiency in DNA DSB repair. (A) Radiation survival curves for the granulocyte/macrophage colony-forming units (CFU-GM) in the bone marrow of wild type (WT), Ku70$^{-/-}$, and Ku80$^{-/-}$ mice (30, 32). (B) Deficiency in the repair of radiation-induced DSB in Ku70$^{-/-}$ and Ku80$^{-/-}$ cells (31). Upper panel shows rejoining of DNA DSB produced by 40 Gy X-ray; (C) Induction of DNA DSB as a function of the radiation dose in WT, Ku70$^{-/-}$ and Ku80$^{-/-}$ cells. Symbols are • for WT, ▲ for Ku70$^{-/-}$, and ■ for Ku80$^{-/-}$ cells, respectively.

Development of B Lymphocyte, but not T Lymphocyte, is Blocked at Early Stage in $Ku70^{-/-}$ Mice Examination of various organs from $Ku70^{-/-}$ mice showed abnormalities only in the lymphoid system (FIG. 2A). Spleen and lymph nodes were disproportionately smaller by 5–10 fold relative to controls. In particular, splenic white pulp nodules were significantly reduced. Immunohistochemistry on deparaffinized tissue sections revealed that the splenic white pulp contained cells that stained with anti-CD3 (i.e., CD3 positive T cells), but there were no CD19 positive B cells (FIG. 2A, panels k and n). The $Ku70^{-/-}$ thymus was also disproportionately smaller and contained 100-fold fewer lymphocytes than $Ku70^{+/+}$ littermates ($2 \times 10^6$ in the former versus $2 \times 10^8$ in the latter; measured in 3 mice of each genotype). In contrast to the $Ku80^{-/-}$ mice, the $Ku70^{-/-}$ thymus displayed normal appearing cortical-medullary junctions (FIG. 2A, panels g and j). Overall, the lymphoid tissues and organs of $Ku70^{-/-}$ mice are somewhat disorganized and much smaller than $Ku70^{+/+}$ mice (Table I); yet, they are relatively more developed and slightly larger than in $Ku80^{-/-}$ mice.

TABLE 1

Lymphoid Cellularity of Ku70-/- Mice

| Tissue and genotype | Cell content (×1 million) Total | Cell content (×1 million) B220+ | Cell content (×1 million) CD4+ CD8+ |
|---|---|---|---|
| Thymus | | | |
| wild type (n =4) | 155 +/− 42 | — | 104 +/− 28 |
| Ku70−/− (n = 3) | 2.98 +/− 0.91 | — | 0.6 +/− 0.2 |
| Ku80−/− (n = 2) | 1.0 +/− 0.5 | — | — |
| Bone Marrow | | | |
| wild type (n = 4) | 11.9 +/− 3.3 | 5.5 +/− 1.5 | — |
| Ku70−/− (n = 3) | 7.2 +/− 2.9 | 1.1 +/− 0.4 | — |
| Ku80−/− (n = 2) | 9.0 +/− 3.0 | — | — |

TABLE 1-continued

Lymphoid Cellularity of Ku70-/- Mice

| Tissue and genotype | Cell content (×1 million) Total | Cell content (×1 million) B220+ | Cell content (×1 million) CD4+ CD8+ |
|---|---|---|---|
| Spleen | | | |
| wild type (n = 4) | 53 +/- 20 | 29 +/- 11 | — |
| Ku70-/- (n = 3) | 6.5 +/- 1.3 | 0.4 +/- 0.2 | — |
| Ku80-/- (n = 2) | 1.2 +/- 0.5 | — | — |

Data shown are arithmetic means ± standard deviations from 2–4 individuals of each genotype analyzed at 4 to 6 weeks of age. Cell numbers are shown per femur for bone marrow, and per whole organ for spleen and thymus.

To further examine the immunological defect in Ku70$^{-/-}$ mice, cells from thymus, bone marrow and spleen were analyzed using monoclonal antibodies specific for lymphocyte surface markers and flow cytometry (19). Consistent with the immunohistological data there was a complete block in B-cell development at the B220$^+$CD43$^+$ stage in the bone marrow, and there were no mature B cells in the spleen (FIG. 2B). In contrast, thymocytes developed through the CD4$^+$CD8$^+$ double-positive (DP) stage and matured into CD4$^+$CD8$^-$ and CD4$^-$CD8$^+$ single-positive (SP), TCRβ positive cells (FIGS. 2B, C). In six four-week old Ku70$^{-/-}$ mice analyzed, the percentage of CD4$^-$CD8$^-$ double-negative thymocytes ranged from 11–62%, and the CD4$^+$CD8$^+$ DP cells varied from 35, 73%. CD4$^-$CD8$^+$(1–11%) and CD4$^+$CD8$^-$(1–3%) SP cells were also detected in the thymus. Furthermore, CD4$^+$CD8$^-$ or CD4$^-$CD8$^+$, single-positive T cells were found in the spleen in 67% of the mice studied (FIG. 2B), which expressed surface TCRβ(FIG. 2C) and CD3. Thus, in contrast to the early arrest of both T- and B- cell development in Ku80$^{-/-}$ mice (FIG. 2B), lack of Ku70 is compatible with the maturation of T cells.

T-cell Receptor and Immunoglobulin Gene Rearrangement

To determine whether a null mutation in Ku70 affects antigen-receptor gene recombination, DNA from bone marrow was amplified with primers specific to immunoglobulin D-J$_H$ and V-DJ$_H$ rearrangements and DNA from thymus was amplified with primers that detected V-DJ$_β$ and D$_δ$-J$_δ$ rearrangements (20, 25–28). FIG. 3A shows that Ku70$^{-/-}$ B cells do undergo D-J$_H$ recombination, at a level which is similar to Ku80$^{-/-}$ B cells, but is 2- to 3-fold lower than the level found in scid mice, and 10–50-fold lower than wild type littermates. It is possible that some, but not all, of the decrease in D-J$_H$ rearrangement is due to a lower fraction of B-lineage cells in the mutant sample, since the wild type littermate mice have only ~5-fold more B220$^+$ cells than the Ku70$^{-/-}$ mice (see Table I). V-DJ$_H$ rearrangements were not detected in either Ku70$^{-/-}$, Ku80$^{-/-}$, or scid bone marrow samples, possibly accounting for the absence of mature B cells in these mutant mice (FIG. 3A).

Figure 3:
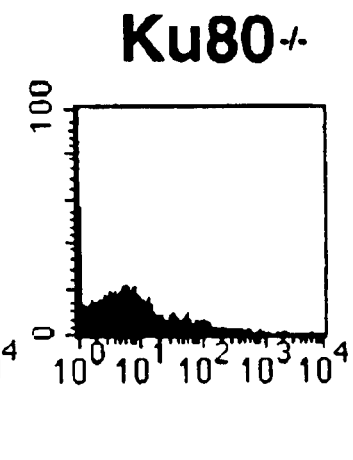
Figure 3B:
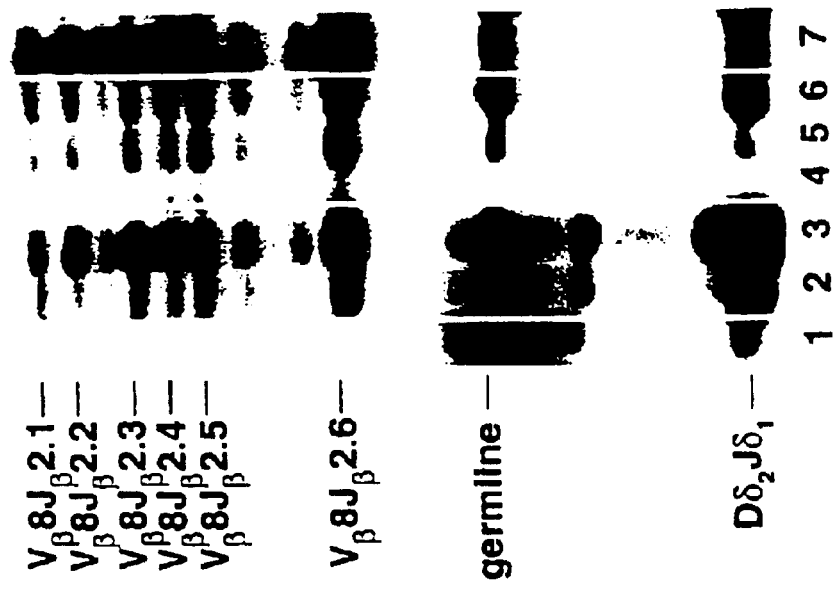
Figure 3A:
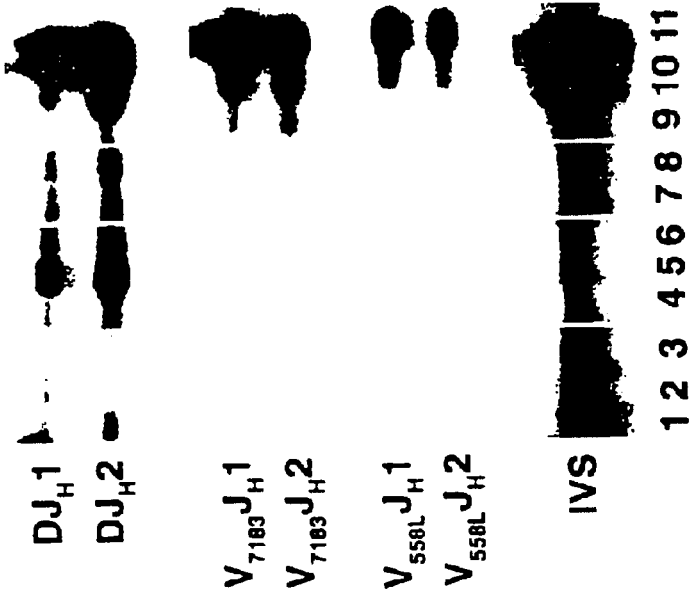

In contrast to the immunoglobulin heavy chain gene recombination, semiquantitative PCR analysis of thymocyte DNA for V-DJ$_β$ joints showed normal levels of TCR$_β$ rearrangements on a per cell basis (FIG. 3B). Similarly, D$_δ$2 and J$_δ$1 coding joints were found in Ku70$^{-/-}$ thymocytes at levels that resembled the wild type. To determine the molecular nature of the amplified coding joints, cloned V$_β$8-DJ$_β$2.6 joints were sequenced. We found normal numbers of N, and P nucleotides as well as normal levels of coding end deletions (FIG. 14). Thus, coding joints in Ku70$^{-/-}$ thymocytes differ from coding joints produced in xrs6 Ku80-deficient cells in that there were no large aberrant deletions (4, 18). We conclude that TCR V(D)J recombination in vivo does not require Ku70.

Figure 4B:
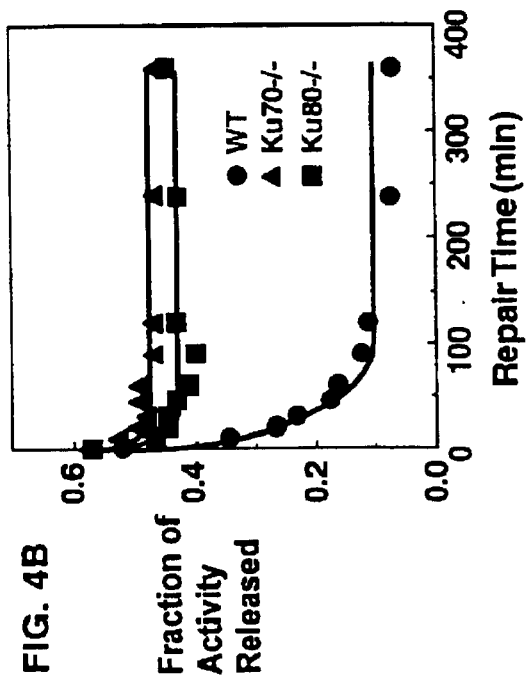
Figure 4C:
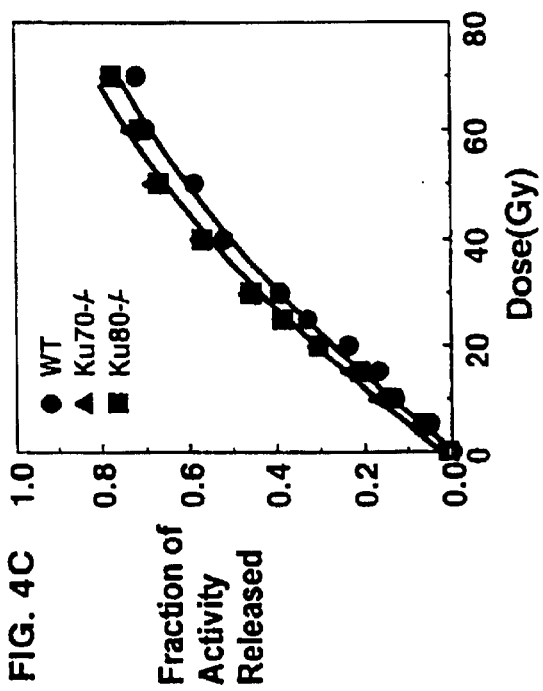
Figure 4A:
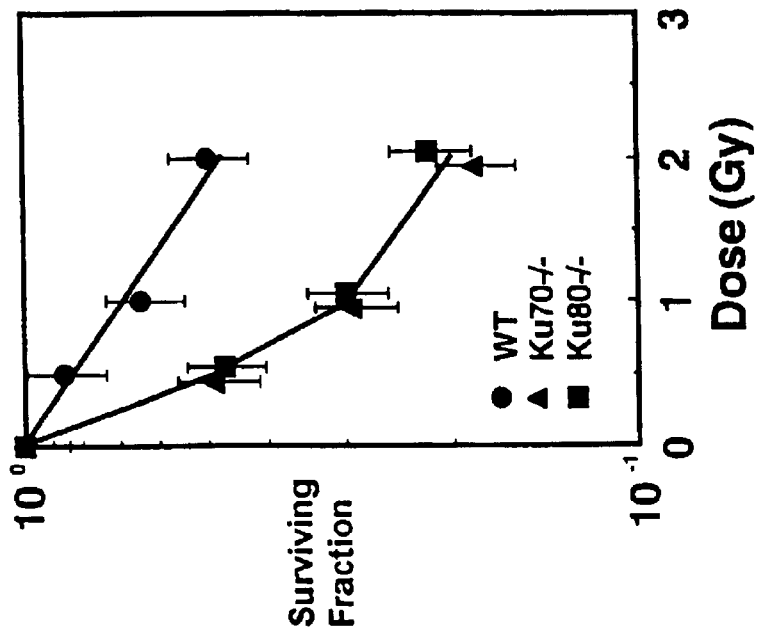

Absence of Ku70 Confers Radiation Hypersensitivity and Deficiency in DNA DSB Repair To assess radiation sensitivity in the absence of Ku70, cells from the bone marrow were exposed to ionizing radiation, and were assayed for colony formation (30, 32). FIG. 4A shows the survival curves of the granulocyte/macrophage colony forming units (CFU-GM) from Ku70$^{-/-}$, Ku80$^{-/-}$ and wild type control mice. CFU-GM from Ku70-deficient mice were more sensitive to ionizing radiation than those from Ku-proficient control mice (FIG. 4A). Similar hypersensitivity to radiation was seen for Ku80$^{-/-}$ CFU-GM (FIG. 4A).

The rate and extent of rejoining of X-ray-induced DNA DSB in Ku70$^{-/-}$, Ku80$^{-/-}$ and Ku70$^{+/+}$ cells were measured using asymmetric field inversion gel electrophoresis (AFIGE) (31). Fibroblasts derived from 13.5-day embryos were exposed to 40 Gy of X-rays and returned to 37° C. for repair. At various times thereafter cells were prepared for AFIGE to quantitate DNA DSB (FIG. 4B, upper panel). DNA DSB were nearly completely rejoined in wild type cells within about 2 h after radiation exposure. However, fibroblasts derived from Ku70$^{-/-}$ mice showed a drastically reduced ability to rejoin DNA DSB. A similar deficiency in DNA DSB rejoining was also observed in fibroblasts derived from Ku80$^{-/-}$ embryos. Despite the large differences observed in rejoining of DNA DSB between wild type fibroblasts and fibroblasts derived from Ku70$^{-/-}$ or Ku80$^{-/-}$ mouse embryos, dose-response experiments showed that Ku70$^{-/-}$, Ku80$^{-/-}$ and wild type fibroblasts were equally susceptible to X-ray-induced damage (FIG. 4B, lower panel). Thus, Ku deficiency affects primarily the ability of cells to rejoin radiation-induced DNA DSB without significantly affecting the induction of DNA damage.

Experimental Discussion

Absence of Ku70 results in radiation hypersensitivity, proportional dwarfism, as well as deficiencies in DNA DSB repair and V(D)J recombination. Thus, Ku70$^{-/-}$ mice resemble Ku80$^{-/-}$ mice in several respects but the two mutations differ in their effects on T and B cell development. Lack of Ku70 was compatible with TCR gene rearrangement and development of mature CD4$^+$CD8$^-$ and CD4$^-$CD8$^+$ T cells, whereas mature T cells were absent in Ku80$^{-/-}$ mice. In contrast, B cells failed to complete antigen receptor gene rearrangement and did not mature in either Ku70$^{-/-}$ or Ku80$^{-/-}$ mice.

What could account for the differences we find in TCR and immunoglobulin gene rearrangements in the Ku70$^{-/-}$ mice? One implication of our findings is that there are alternative Ku70-independent rescue pathways that are compatible with completion of V(D)J recombination in T cells. It is likely at the critical phase of T cell maturation, other DNA repair activity may be stimulated (33, 34) and can functionally complement the Ku70 gene in T cell-specific V(D)J recombination. Since Ku80$^{-/-}$ mice are deficient in both T and B lymphocyte development, it is plausible that these yet to be identified alternative DNA repair pathways include Ku80. The much reduced level of Ku80 protein in Ku70$^{-/-}$ cells may in part account for the hypocellularity of Ku70$^{-/-}$ thymii.

Although the role of Ku in V(D)J recombination is not molecularly defined, Ku has been proposed to protect DNA ends from degradation (18, 35), to activate DNA-PK (10, 11), and to dissociate the RAG/DNA complex to facilitate the joining reaction (20). These functions are not mutually exclusive, and they are all dependent on the interaction of Ku with DNA. Thus, the finding that Ku70 is not required for TCR gene rearrangement is particularly unexpected, because the Ku70 subunit is believed to be the DNA-binding subunit of the Ku complex (36), and DNA-end binding activity was not detected in Ku70-deficient cells (FIG. 1D).

In summary, our studies provide direct evidence supporting the involvement of Ku70 in the repair of DNA DSB and V(D)J recombination, and the presence of a Ku70-independent rescue pathway(s) in TCR V(D)J rearrangement. The distinct phenotype of Ku70$^{-/-}$ mice should make them valuable tools for unraveling the mechanism(s) of DNA repair and recombination.

References for the First Series of Experiments

1. Li, Z., T. Otevrel, Y. Gao, H.-L. Cheng, B. Sneed, T. Stamato, G. Taccioli, and F. W. Alt. 1995. The XRCC4 gene encodes a novel protein involved in DNA double-strand break repair and V(D)J recombination. *Cell* 83: 1079–1089.
2. Hendrickson, E. A., X.-Q. Qin, E. A. Bump, D. G. Schatz, M. Oettinger, and D. T. Weaver. 1991. A link between double-strand break-related repair and V(D)J recombination: The scid mutation. *Proc. Natl. Acad. Sci. USA* 88: 4061–4065.
3. Pergola, F., M. Z. Zdzienicka, and M. R. Lieber. 1993. V(D)J recombination in mammalian cell mutants defective in DNA double-strand break repair. *Mol. Cell. Biol.* 13: 3464–3471.
4. Taccioli, G. E., G. Rathbun, E. Oltz, T. Stamato, P. A. Jeggo, and F. W. Alt. 1993. Impairment of V(D)J recombination in double-strand break repair mutants. *Science* 260: 207–210.
5. Roth, D. B., T. Lindahl, and M. Gellert. 1995. *Curr. Biol.* 5: 496.
6. Bogue, M., and D. B. Roth. 1996. *Current Opinions in Cell Biol* 8: 175.
7. Jeggo, P. A., G. A. Taccioli, and S. P. Jackson. 1995. Menage a trois: double strand break repair, V(D)J recombination and DNA-PK. *BioEssays* 17: 949–956.
8. Weaver, D. T. 1995. What to do at an end: DNA double-strand-break repair. *TIGS* 11: 388–392.
9. Biedermann, K. A., J. Sun, A. J. Giaccia, L. M. Tosto, and J. M Brown. 1991. scid mutation in mice confers hypersensitivity to ionizing radiation and a deficiency in DNA double-strand break repair. *Proc. Natl. Acad. Sci. USA* 88: 1394–1397.
10. Dvir, A., S. R. Peterson, M. W. Knuth, H. Lu, and W. S. Dynan. 1992. Ku autoantigen is the regulatory component of a template-associated protein kinase that phosphorylates RNA polymerase II. *Proc. Natl. Acad. Sci. USA* 89: 11920–11924.
11. Gottlieb, T. M., and S. P. Jackson. 1993. The DNA-dependent protein kinase: requirement for DNA ends and association with Ku antigen. *Cell* 72: 131–142.
12. Lees-Miller, S. P. 1996. The DNA-dependent protein kinase, DNA-PK: 10 years and no ends in sight. *Biochem. Cell Biol.* 74: 503–512.
13. Peterson, S. R., A. Kurimasa, M. Oshimura, W. S. Dynan, E. M. Bradbury, and D. J. Chen. 1995. Loss of the catalytic subunit of the DNA-dependent protein kinase in DNA double-strand-break-repair mutant mammalian cells. *Proc. Natl. Acad. Sci. USA* 92: 3171–3174.
14. Kirchgessner, C. U., C. K. Patil, J. W. Evans, C. A. Cuomo, L. M. Fried, T. Carter, M. A. Oettinger, and J. M. Brown. 1995. DNA-dependent kinase (p350) as a candidate gene for the murine SCID defect. *Science* 267: 1178–1183.
15. Blunt, T., N. J. Finnie, G. E. Taccioli, G. C. M. Smith, J. Demengeot, T. M. Gottlieb, R. Mizuta, A. J. Varghese, F. W. Alt, P. A. Jeggo, and S. P. Jackson. 1995. Defective DNA-dependent protein kinase activity is linked to V(D)J recombination and DNA repair defects associated with the murine scid mutation. *Cell* 80: 813–823.
16. Boubnov, N. V., K. T. Hall, Z. Wills, S. E. Lee, D. M. He, D. M. Benjamin, C. R. Pulaski, H. Band, W. Reeves, E. A. Hendrickson, and D. T. Weaver. 1995. Complementation of the ionizing radiation sensitivity, DNA end binding, and V(D)J recombination defects of double-strand break repair mutants by the p86 Ku autoantigen. *Proc. Natl. Acad. Sci. USA* 92: 890–894.
17. Smider, V., W. K. Rathmell, M. R. Lieber, and G. Chu. 1994. Restoration of x-ray resistance and V(D)J recombination in mutant cells by Ku cDNA. *Science* 266: 288–291.
18. Taccioli, G. E., T. M. Gottlieb, T. Blunt, A. Priestly, J. Demengeot, R. Mizuta, A. R. Lehmann, F. A. Alt, S. P. Jackson, and P. A. Jeggo. 1994. Ku80: product of the XRCC5 gene and its role in DNA repair and V(D)J recombination. *Science* 265: 1442–1445.
19. Nussenzweig, A., C. Chen, V. da Costa Soares, M. Sanchez, K. Sokol, M. C. Nussenzweig, and G. C. Li. 1996. Requirement for Ku80 in growth and immunoglobulin V(D)J recombination. *Nature* (London) 382: 551–555.
20. Zhu, C., M. A. Bogue, D.-S. Lim, P. Hasty, and D. B. Roth. 1996. Ku86-deficient mice exhibit severe combined immunodeficiency and defective processing of V(D)J recombination intermediates. *Cell* 86: 379–389.
21. Takiguchi, Y., A. Kurimasa, F. Chen, P. E. Pardington, T. Kuriyama, R. T. Okinaka, R. Moyzis, and D. J. Chen. 1996. Genomic structure and chromosomal assignment of the mouse Ku70 gene. *Genomics* 35: 129–135.
22. Kim, D., H. Ouyang, S.-H. Yang, A. Nussenzweig, P. Burgman, and G. C. Li. 1995. A constitutive heat shock element-binding factor is immunologically identical to the Ku-autoantigen. *J. Biol. Chem.* 270: 15277–15284.
23. Serrano, M., H.-W. Lee, L. Chin, C. Cordon-Cardo, D. Beach, and R. A. DePinho. 1996. Role of the INK4a in tumor suppression and cell mortality. *Cell* 85: 27–37.
24. Cordon-Cardo, C., and V. M. Richon. 1994. Expression of the retinoblastoma protein is regulated in normal human tissue. *Am. J. Pathol.* 144: 500–510.
25. Ausubel, F. M., R. Brent, R. E. Kingston, D. D. Moore, J. G. Seidman, J. A. Smith, and K. Struhl. 1997. Current Protocols in Molecular Biology. John Wiley & Sons, New York.
26. Costa, T. E. F., H. Suh, and M. Nussenzweig. 1992. Chromosomal position of rearranging gene segments influences allelic exclusion in transgenic mice. *Proc. Natl. Acad. Sci. USA* 89: 2205–2208.
27. Roth, D. B., C. Zhu, and M. Gellert. 1993. Characterization of broken DNA molecules associated with V(D)J recombination. *Proc. Natl. Acad. Sci. USA* 90: 10788–10792.
28. Bogue, M. A., C. Zhu, E. Aguilar-Cordova, L. A. Donehower, and D. B. Roth. 1996. p53 is required for both radiation-induced differentiation and rescue of V(D)J rearrangement in scid mouse thymocytes. *Genes Dev.* 10: 553–565.
29. Van Zant, G., D. Flentje, and M. Flentje. 1983. The effect of hyperthermia on hemopoietic progenitor cells of the mouse. *Radiat. Res.* 95: 142–149.
30. Mivechi, N. F., and G. C. Li. 1985. Thermotolerance and profile of protein synthesis in murine bone marrow cells after heat shock. *Cancer Res.* 45: 3843–3849.

31. Illiakis, G., L. Metzger, N. Denko, and T. D. Stamato. 1991. Detection of DNA double-strand breaks in synchronous cultures of CHO cells by means of asymmetric field inversion gel electrophoresis. *Int. J. Radiat. Biol.* 59: 321–341.
32. Fulop, G. M., and R. A. Phillips. 1990. The scid mutation in mice causes a general defect in DNA repair. *Nature* (London) 347: 479–482.
33. Strasser, A., A. W. Harris, L. M. Corcoran, and S. Cory. 1994. Bcl-2 expression promotes B- but not T-lymphoid development in scid mice. *Nature* (London) 368: 457–460.
34. Danska, J. S., F. Pflumio, C. J. Williams, O. Huner, J. E. Dick, and C. J. Guidos. 1994. Rescue of T cell-specific V(D)J recombination in SCID mice by DNA-damaging agents. *Science* 266: 450–455.
35. Liang, F., and M. Jasin. 1996. Ku80-deficient cells exhibit excess degradation of extrachromosomal DNA. *J. Biol. Chem.* 271: 14405–14411.
36. Chou, C. H., J. Wang, M. W. Knuth, and W. H. Reeves. 1992. Role of a major autoepitope in forming the DNA binding site of the p70 (Ku) antigen. *J. Exp. Med.* 175: 1677–1684.

Second Series of Experiments

Recent investigations have linked the molecular mechanisms of two processes, the repair of radiation-induced DNA double-strand breaks (DSB) and V(D)J recombination during T- and B-cell development. The mammalian DNA-dependent protein kinase DNA-PK has emerged as a key molecule in these pathways. DNA-PK is a serine/threonine kinase that consists of a 465-kDa catalytic subunit (DNA-PKcs), and a DNA-targeting heterodimer consisting of a 70-kDa and an 86-kDa polypeptides (termed the Ku70 and Ku80, respectively). When assembled on double-stranded DNA in vitro, the DNA-PK holoenzyme phosphorylates transcription factors and other proteins, including Sp1, Oct1, c-fos, c-jun, p53 and the 34-kDa subunit of replication protein A (Anderson, 1993; Pan, 1994). Genetic and biochemical studies strongly suggest a critical role for DNA-PK in DSB repair and V(D)J recombination (Jackson, 1995; Jeggo, 1995; Lees-Miller, 1996). Cell lines lacking either Ku80 or DNA-PKcs are defective in both DSB repair and V(D)J recombination, and are hypersensitive to ionizing radiation (Blunt, 1995; Jackson, 1995; Jeggo, 1995; Kirchgessner, 1995; Peterson, 1995; Rathmell, 1994; Smider, 1994; Taccioli, 1994). Genes encoding each of the subunits of DNA-PK have been mapped to loci that complement the defect in x-ray-sensitive mutant cells (Jeggo, 1995; Thompson, 1995). The gene encoding DNA-PKcs maps to human chromosome 8q11, which is also identified as the locus of the SCID gene (severe combined immune deficiency) (Blunt, 1995; Kirchgessner, 1995; Sipley, 1995). Cells derived from SCID mice are hypersensitive to x-ray, defective in DSB repair and V(D)J recombination (Biedermann, 1991), and lack DNA-PKcs expression (Blunt, 1995; Kirchgessner, 1995; Peterson, 1995). Consistent with these findings, a radiosensitive human glioma cell line was found to be defective in DSB repair and devoid of DNA-PKcs mRNA and proteins (Lees-Miller, 1995).

The Ku heterodimer was first discovered as an autoantigen in patients with autoimmune disorders (Mimori, 1981). Genes encoding Ku70 and Ku80 have been cloned and cytogenetically mapped to the human chromosomes 22q13 and 2q33–35, (Cai, 1994). The groups of Dynan and Jackson have provided evidence that Ku is the DNA-targeting subunit of DNA-PK (Dvir, 1992; Gottlieb, 1993). Alone, neither DNA-PKcs nor Ku has kinase activity, and DNA-PK activity requires the assembly of approximately equimolar amounts of Ku70, Ku80 and DNA-PKcs on double-stranded DNA (Chan, 1996; Suwa, 1994).

Despite the rapid advances in our understanding of the genetics of the DNA-PK subunits, the precise function of each of these proteins in vivo, and their roles in DSB repair and V(D)J recombination remain unclear. Several models have been postulated (Jackson and Jeggo, 1995, Lees-Miller, 1996). After localization to a DSB, DNA-PK may signal via phosphorylation to activate enzymes or other factors involved in the rejoining of DNA ends. Alternatively, perhaps in addition to its function in signaling, DNA-PK may structurally tether adjacent DNA ends in a conformation suitable for subsequent end rejoining (Jeggo, et al., 1995, Roth, et al., 1995). Although it remains to be proven, it is very likely that the protein kinase activity of DNA-PK plays a critical role in DNA repair and recombination (Jackson and Jeggo, 1995, Lees-Miller, 1996). The in vivo function of Ku is also not well defined at the molecular level. Ku has been proposed to protect DNA ends from degradation (Liang and Jasin, 1996, Taccioli, et al., 1994), to activate DNA-PK (Dvir, et al., 1992, Gottlieb and Jackson, 1993) and to dissociate the RAG/DNA complex to facilitate DNA joining reaction (Zhu, et al., 1996). These functions are not mutually exclusive, and they all appear to depend on the interaction of Ku with DNA molecules.

To facilitate studies on the function of the Ku subunits of DNA-PK in vivo, we have recently carried out targeted disruption of Ku70 and Ku80 genes in mice (Nussenzweig, et al., 1996, Ouyang, et al., 1997). In Ku80$^{-/-}$ mice, the development of both T- and B-lymphocyte is arrested at early progenitor stages, and there is a profound deficiency in V(D)J rearrangement (Nussenzweig, et al., 1996, Zhu, et al., 1996). Similar to Ku80$^{-/-}$ phenotype, inactivation of Ku70 leads to impaired B-lymphocyte development and deficient DSB repair (Ouyang, et al., 1997). However, in contrast to the Ku80$^{-/-}$ phenotype, absence of Ku70 does not abrogate T-cell receptor (TCR) gene recombination and the development of mature T-cells (Gu, et al., 1997, Ouyang, et al., 1997). These studies indicate that Ku70 plays an essential role in DSB repair, but is not essential for TCR V(D)J recombination, suggesting that distinct and overlapping pathways may mediate DSB repair and V(D)J recombination. A related implication of these findings is that there may be residual activity or alternate Ku70-independent pathways for V(D)J recombination during T-cell development. Hence, the processing of TCR V(D)J recombination in the Ku70$^{-/-}$ mouse, which is defective in DSB repair, may facilitate the generation of illegitimate recombination events (Cleary, 1991), potentially leading to tumor development.

In the present study, we examined the effect of the Ku70$^{-/-}$ defect relative to malignant transformation and tumor development in mutant mice and derived cell lines. Fibroblasts derived from Ku70$^{-/-}$ mice exhibit significantly higher frequencies of sister chromatid exchanges and spontaneous neoplastic transformation, relative to the wild type controls. Consistent with this cellular phenotype, the majority of Ku70$^{-/-}$ mice developed spontaneous thymic and disseminated T-cell lymphomas by 8 months of age. Lack of Ku70 protein expression was also found in more than 50% of tumor tissue specimens obtained from patients with T-cell lymphomas. Collectively, these findings strongly suggest the Ku70 locus as a candidate tumor suppressor gene for murine and human T-cell lymphomas.

We present evidence that inactivation of the Ku70 gene leads to a propensity for malignant transformation, both in vitro and in vivo. Ku70$^{-/-}$ mouse fibroblasts displayed an increased rate of sister chromatid exchange and a high frequency of spontaneous neoplastic transformation. Ku70$^{-/-}$ mice, known to be defective in B- but not T-lymphocyte maturation, developed thymic and disseminated T-cell lymphomas at a mean age of 6 months, with CD4$^+$CD8$^+$ tumor cells expressing wild type p53. A plausible link between Ku70 abnormality and human T-cell lymphomas was supported by the lack of Ku70 expression in tumor specimens from four out of seven patients analyzed. These findings directly demonstrate that Ku70-deficiency facilitates neoplastic growth and strongly suggest the Ku70 locus as a candidate tumor suppressor gene.

Experimental Results

Further Characterization of the Ku70$^{-/-}$ Mouse

Figure 5A:
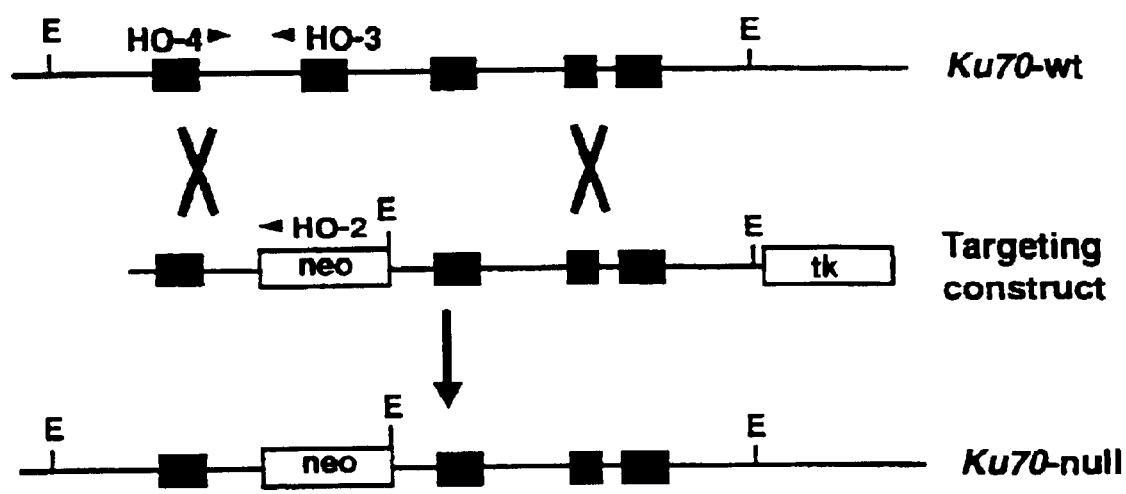

We have recently reported the generation of Ku70$^{-/-}$ mice (Ouyang, et al., 1997). The Ku70 gene was inactivated by deleting 336-bp of exon 2, including the translational initiation codon of the mouse Ku70 locus (FIG. 5A). Ku70$^{-/-}$ heterozygotes exhibited no abnormalities and were used to generate a colony of Ku70$^{-/-}$ mice, used for the current experiments.

Figures 2, 2A, 3, 4, 5:
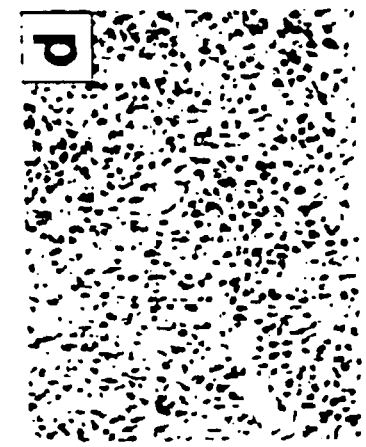
FIG. 5 Disruption of the Ku70 locus in mouse ES cells and generation of Ku70$^{-/-}$ mice. (A) Diagrammatic representation of the Ku70 locus (top), the targeting construct (middle), the targeted allele (bottom) and the PCR primers. EcoRI (E) restriction sites used to detect the targeted genes are indicated. (B) PCR analysis of tail DNA from Ku70$^{+/+}$, Ku70$^{+/-}$, and Ku70$^{-/-}$ mice. The wild type sequence which was amplified using HO-4/HO-3 primers was not present in Ku70$^{-/-}$ mouse tail while the disrupted sequence primed by HO-4/HO-2 was not expressed in Ku70$^{+/+}$ mouse. (C) Postnatal growth of Ku70$^{+/+}$ and Ku70$^{-/-}$ littermates. Average weights of seven animals from each genotype are plotted against time. There was no significant difference in the body weight between Ku70$^{+/+}$ and Ku70$^{+/-}$ mice. (D) Photograph of 5-week-old Ku70$^{+/+}$ and Ku70$^{-/-}$ littermates.
Figure 5B:
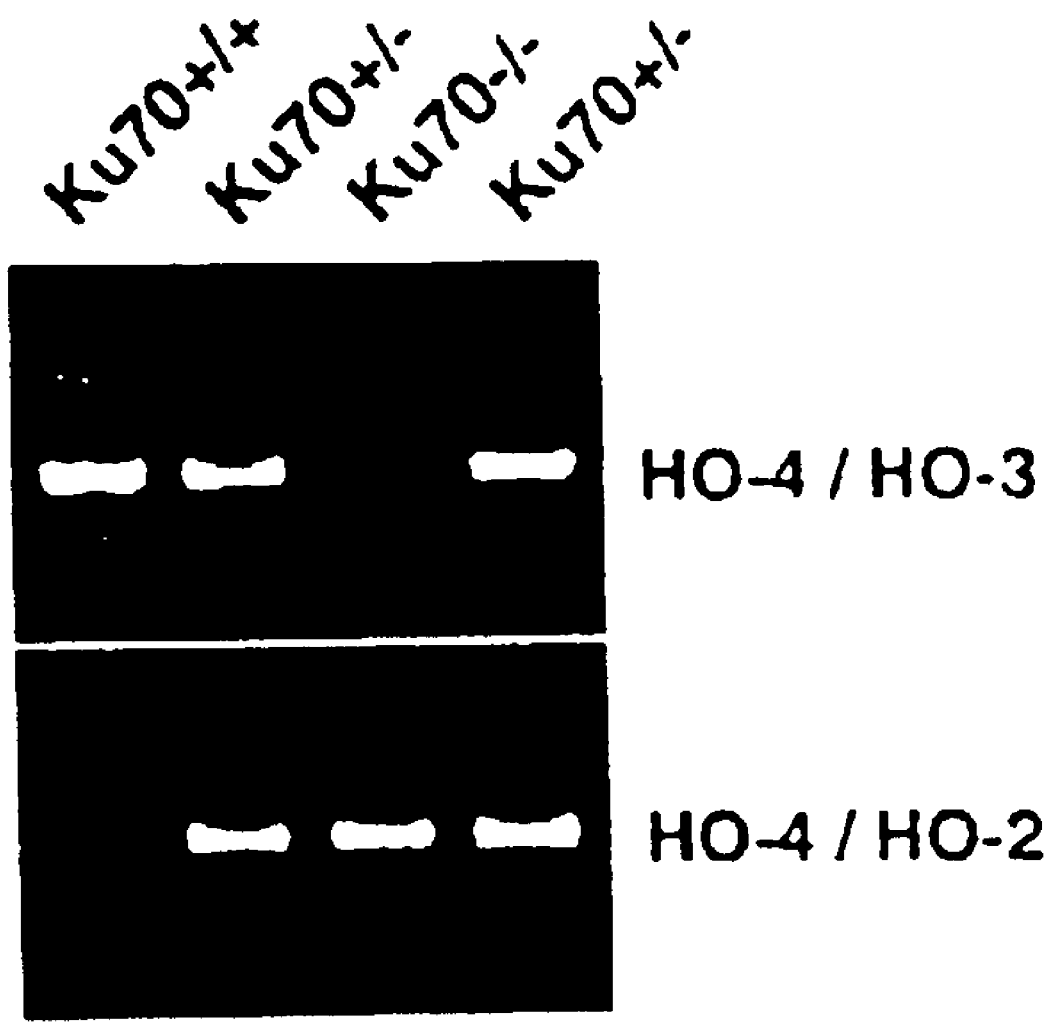
Figure 5D:
Figure 6:
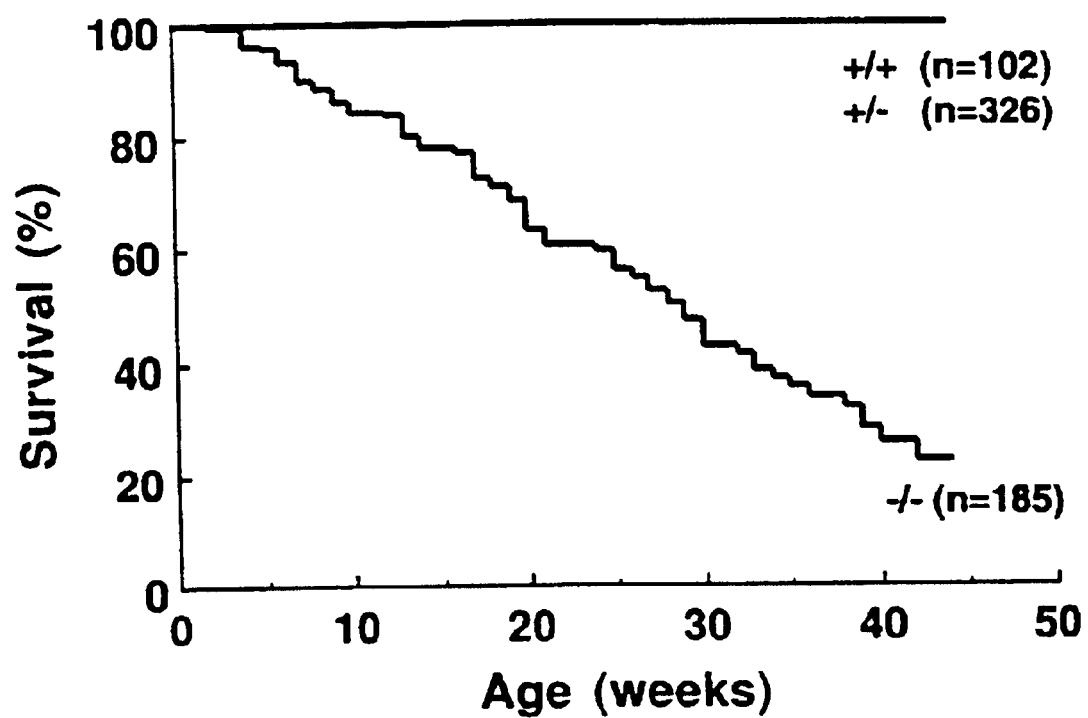

PCR analysis using specific primers confirmed that part of exon 2 was eliminated from the genome of Ku70$^{-/-}$ offsprings (FIG. 5B), and Western blot analysis with anti-Ku70 antibodies demonstrated the absence of Ku70 protein in Ku70$^{-/-}$ cells. Offsprings from Ku70$^{+/-}$ intercrosses were of all three genotypes with approximately 25% being Ku70$^{-/-}$ homozygotes, as expected from a Mendelian distribution. Ku70$^{-/-}$ mice were fertile, but 40–60% smaller than their Ku70$^{+/-}$ and Ku70$^{+/+}$ littermates (FIG. 5C), a phenotype similar to Ku80$^{-/-}$ mice (Nussenzweig, et al., 1996), but distinctly different from that reported for SCID mice (Bosma, et al., 1983, Bosma and Carroll, 1991). The weight differences from the wild-type phenotype were present at birth and maintained through adulthood (FIG. 5C).

Examination of tissues from Ku70$^{-/-}$ mice revealed abnormalities in lymphatic organs and the gastrointestinal tract. Other organs, including brain, lung, liver, heart, kidney, testis and ovaries were proportionally smaller but with no apparent structural or histological abnormalities. Histological examination of the gastrointestinal tract showed mild to severe segmental aganglionosis affecting small intestine and colon (discussed in a later section). The Ku70$^{-/-}$ thymus was disproportionately smaller and contained 50- to 100-fold fewer thymoctyes than Ku70$^{+/+}$ littermates, but displayed relatively normal appearing cortical-medullary junctions, as was previously reported (Ouyang, et al., 1997). The Ku70$^{-/-}$ spleen was also 5- to 10-fold smaller with the splenic white pulp significantly reduced. Immunohistochemical studies and multiparameter flow cytometric analyses revealed that there was a complete block in B-cell development at early progenitor stages. In contrast, absence of Ku70 does not block TCR gene rearrangement and the development of T-cells.

Ku70$^{-/-}$ Mice Develop T-cell Lymphomas

Figures 2, 2A, 3, 4, 5, 6:
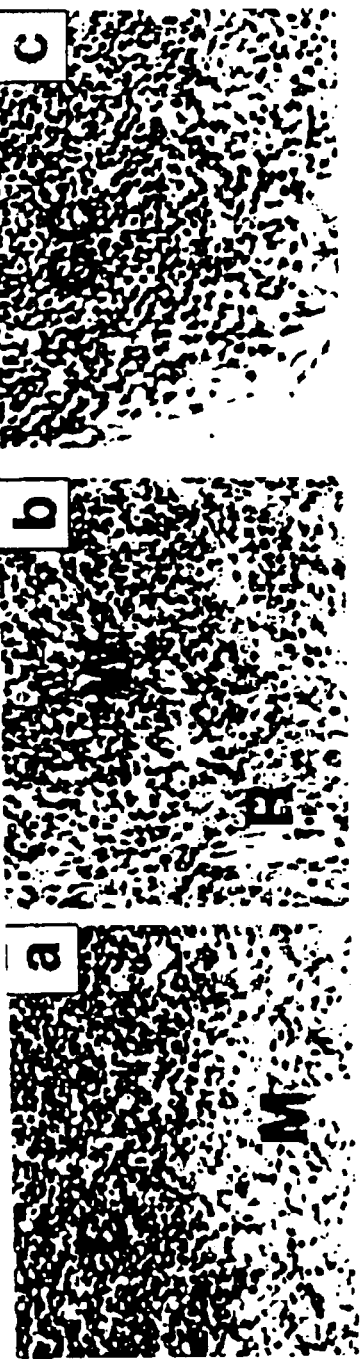
FIG. 6 Survival curves of Ku70$^{+/+}$, Ku70$^{+/-}$, and Ku70$^{-/-}$ mice. Sample sizes used for the statistical analysis (Kaplan and Meier, 1958) are: n (+/+)=102, n (+/-)=326, and n (-/-)=185.
Figure 2C:
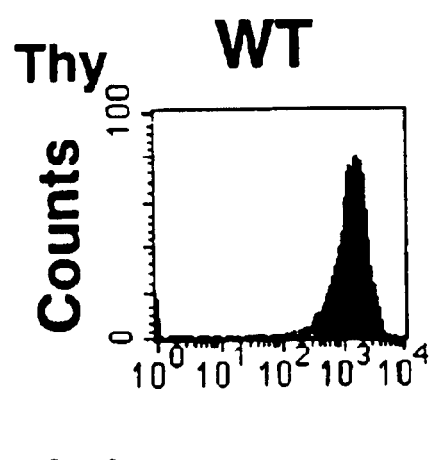
Figure 2:
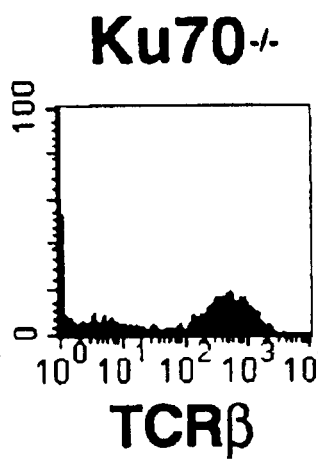
Figure 4:
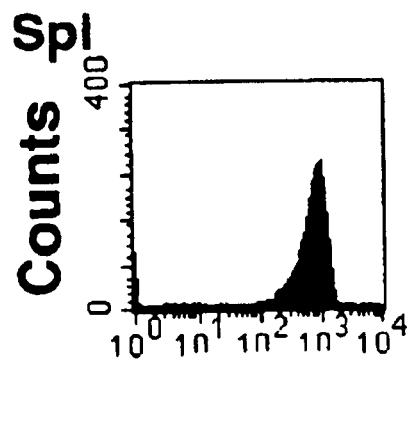
Figure 5:
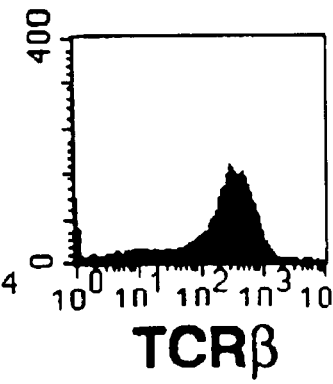
Figure 6:
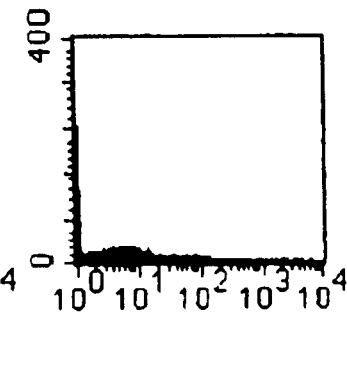

As noted previously, the processing of V(D)J recombination and proliferation of T cell precursors in Ku70$^{-/-}$ mouse, which has an intrinsic defect in DNA DSB repair, may enhance illegitimate recombination and lead to tumor development. To test this hypothesis, the tumor susceptibility of Ku70$^{-/-}$ mice was assessed. We randomly assigned litters arising from heterozygous intercrosses (e.g., Ku70$^{+/+}$, Ku70$^{+/-}$, Ku70$^{-/-}$) for our experiments and monitored the mice daily for tumor development and survival. As shown in FIG. 6, 100% of Ku70$^{+/+}$(n=102) and Ku70$^{+/-}$(n=326) littermates remained tumor-free and survived through the first 45 weeks of life. However, the actuarial survival of the Ku70$^{-/-}$ mice at risk at 42 weeks was only 22.4%, with a median survival of 28 weeks.

Autopsy examinations showed that, in the first 5–18 weeks of life, 14.2% of Ku70$^{-/-}$ mice died of severe forms of a Hirschprung-like syndrome (see below). Subsequently, animals died of thymic and disseminated lymphomas (FIG. 7). The youngest animal with a detectable tumor was 14 weeks old, and by 36 weeks of age, the great majority of the remaining Ku70$^{-/-}$ mice died of lymphoma. Tumors of B lymphoid or non-lymphoid organs were not detected among the 45 tumor-bearing animals examined. In contrast, for the same observation period, no tumors were detected in colonies of Ku80$^{-/-}$ and SCID mice. Histologically, the primary tumors consisted of mononuclear, atypical cells with cleaved nuclei, prominent nucleoli, and many mitotic figures. Immunohistochemical analyses revealed that the tumor cells were CD3$^+$, confirming the diagnosis of T-cell lymphoma (FIGS. 7, D, E, and F). In most cases, these tumors involved other organs, such as the lung, heart, kidney, spleen and liver; a CD3$^+$ phenotype was identified in all of these tumors.

Cell lines were readily established from five thymic tumors, designated T-96, T-49, T-248, T-311, and T-441. These lines had a doubling time of 16–18 hr. Flow cytometric analysis of three of these tumor lines at early passage revealed a CD4$^+$ CD8$^+$ DP phenotype (FIG. 7G), consistent with immature T cells of thymic origin. It is, thus, reasonable to postulate that some DP Ku70$^{-/-}$ cells acquired mutations that enhanced their survival or the ability to proliferate relative to that of short-lived wild type DP thymocytes.

Alterations of the p53 gene occur commonly in many different tumor types, including lymphomas. To determine whether a similar phenotypic profile exists in the Ku70$^{-/-}$ model, we analyzed the level of p53 expression in the T-cell lymphomas developed in the Ku70$^{-/-}$ mice. The normal cellular levels of p53 expression are very low and usually undetectable by immunohistochemical assays. In addition, the half-life of p53 protein is short, ranging from 5 to 20 minutes (Levine, 1997). However, in tumors bearing dominant-negative mutations of p53, stabilization of the mutant protein leads to an accumulation of the protein in the nuclei of tumor cells that can be readily detected by immunohistochemical methods (Cordon-Cardo, et al., 1994). In all Ku70$^{-/-}$ T-cell lymphomas and their derived cell lines studied, we found undetectable levels of p53 expression. Therefore, it can be concluded that the wild type status of the p53 gene is maintained in these murine T-cell lymphomas.

Ku70$^{-/-}$ Fibroblasts also Undergo Malignant Transformation

Figure 8A:
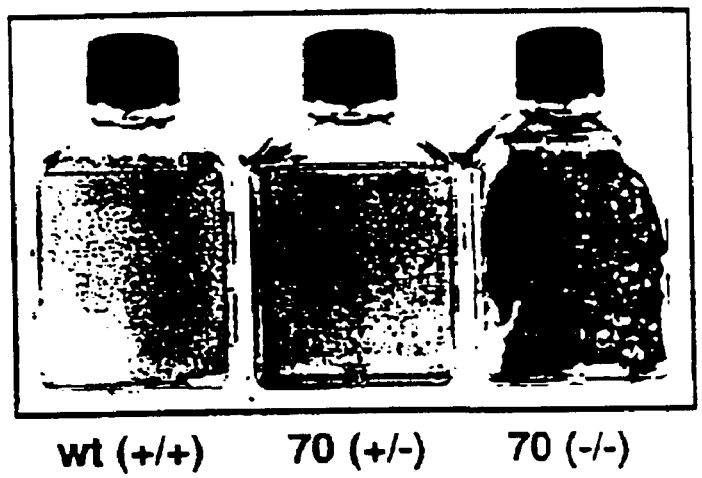
FIG. 8 Neoplastic transformation of Ku70$^{-/-}$ early-passage mouse ear fibroblasts (MEFs). (A) Focus-formation assay. (B) Morphology of transformed foci (type III). (C) Colony-formation assay in soft agar. Left, wild type (Ku70$^{+/+}$) MEFs untransformed; middle left, Ku70$^{-/-}$ MEFs untransformed; middle right (focus T1), cells from a focus produced by spontaneous transformation of Ku70$^{-/-}$ MEFs (passage 7); and right (focus C2), cells from a focus produced by transformation of E6/E7 co-transfected Ku70$^{-/-}$ MEFs. Cells from other randomly chosen foci were also able to produce colonies in soft agar.
Figure 8B:
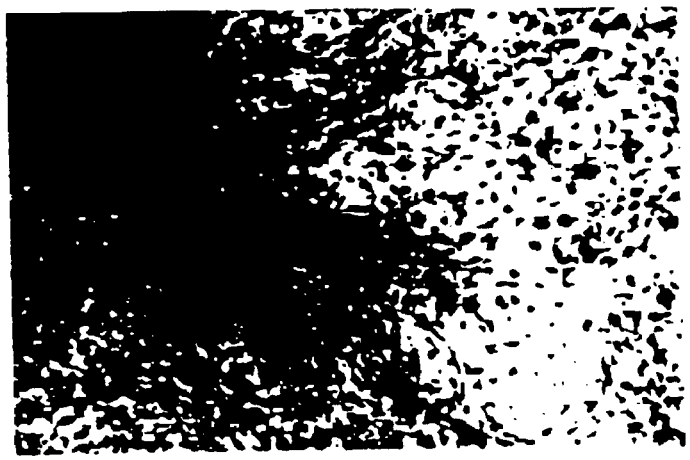

Spontaneous neoplastic transformation occurs rarely in primary mouse fibroblasts. Consistent with this observation, primary mouse ear fibroblasts (MEFs), derived from Ku70$^{+/+}$ or Ku70$^{+/-}$ and cultured up to passage 10, did not undergo spontaneous malignant transformation. In contrast, the formation of type III transformed foci was observed in Ku70$^{-/-}$ MEFs at a transformation frequency of $4.3 \times 10^{-2}$/viable cell (FIGS. 8, A and B). Co-transfection with HPV16 E6 and E7 into Ku70$^{-/-}$ MEFs further increased the frequency of foci formation, whereas transformation was not observed in E6/E7 co-transfected Ku70$^{+/+}$ or Ku70$^{+/-}$ fibroblasts.

Analysis of chromosomal aberrations in the various cell cultures grown at 37° C. revealed that the Ku70$^{-/-}$ cells contained 0.326 sister chromatid exchanges (SCE) per chromosome (n=30 cells), representing a 2.2-fold increase over that of Ku70$^{-/-}$ cells (0.147 SCE per chromosome, n=34 cells) (p<0.05). Similarly, the E6/E7 co-transfected Ku70$^{-/-}$ cells contained a nearly 3-fold higher frequency of SCE (0.262 SCE per chromosome, n=36 cells) than the E6/E7 co-transfected Ku70$^{+/+}$ or wild type Ku70$^{+/+}$ cells (0.092 SCE per chromosome, n=23 cells) (p<0.05).

Figure 8C:
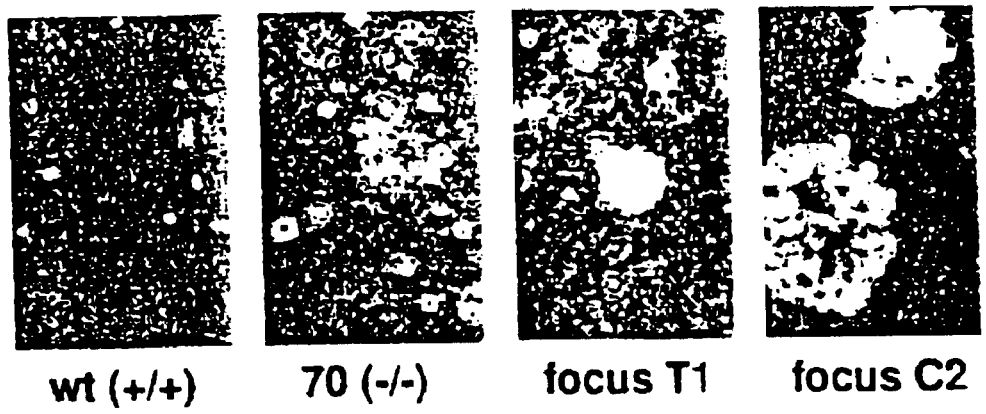

The foci derived from the primary and from the E6/E7 co-transfected Ku70$^{-/-}$ cultures were further tested for their ability to grow under anchorage-independent conditions. FIG. 8C shows that Ku70$^{-/-}$ cells derived from the transformed foci readily produced colonies in soft agar, while no anchorage-independent growth was evident for the Ku70$^{+/+}$ cells. Taken together, these results indicate that Ku70-deficiency leads to an increased propensity for malignant transformation of primary mouse fibroblasts.

Extreme Radiation Sensitivity of Ku70$^{-/-}$ Mice and Ku70$^{-/-}$ Fibroblasts

We have shown previously that Ku70$^{-/-}$ primary fibroblasts were impaired in the repair of radiation-induced DSB (Ouyang, et al., 1997). To demonstrate that this deficiency in DSB repair leads to the hypersensitivity of Ku70$^{-/-}$ cells to radiation, monolayers of Ku70$^{-/-}$ and Ku70$^{+/+}$ primary ear fibroblasts (passage 7) were exposed to graded doses of γ-irradiation (0–6 Gy), and survival was determined by a colony formation assay. FIG. 9A clearly shows that Ku70$^{-/-}$ cells were much more radiosensitive than the wild type controls, with a >100-fold difference in survival after 400 cGy of γ-irradiation.

Figure 9B:
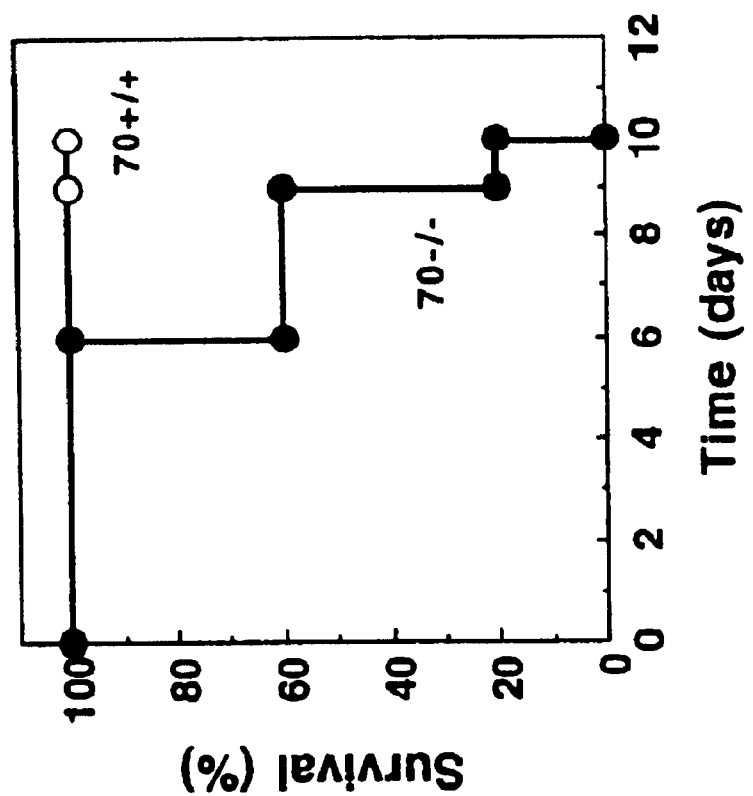
FIG. 9 Radiation sensitivity of Ku70$^{-/-}$ fibroblasts and Ku70$^{-/-}$ mice. (A) Ku70$^{-/-}$ and wild-type Ku70$^{+/+}$ primary ear fibroblasts (passage 7) were exposed to graded doses of Y-irradiation. Ku70-deficient cells show significantly decreased ability to form colonies after ionizing radiation as compared with the wild-type cells. (B) Survival of Ku70$^{-/-}$ and wild-type mice irradiated with 400 cGy. Five adult mice (4 months old) from each genotype were irradiated simultaneously and monitored for 2 weeks. Whereas all of the wild-type mice survived, 100% of the Ku70$^{-/-}$ mice died within this period.
Figure 9A:
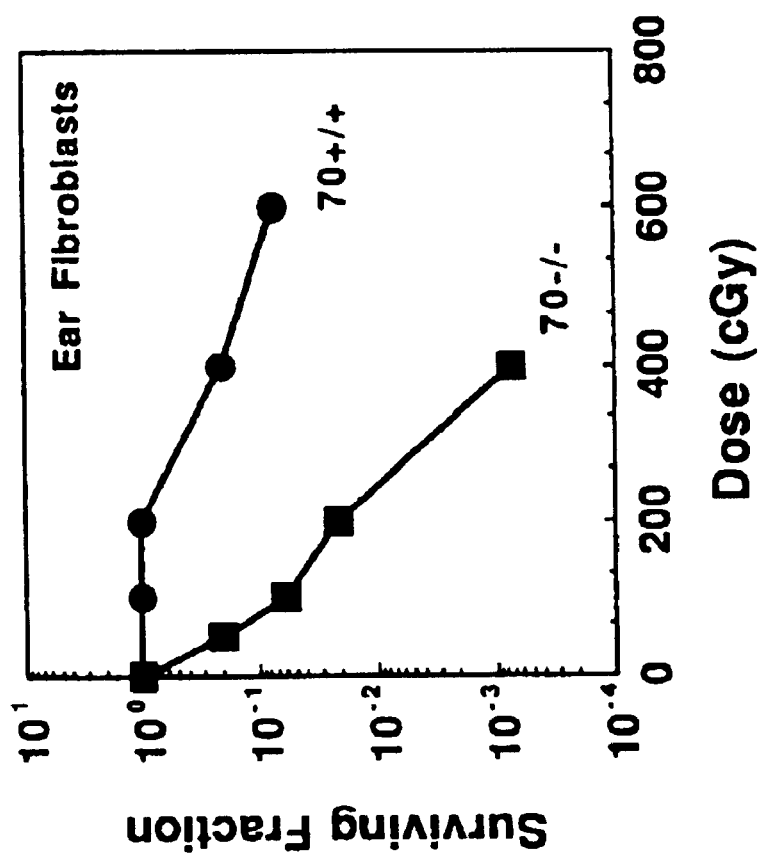

To assess the radiation-sensitive phenotype in vivo, adult (4 months old) Ku70$^{-/-}$ mice were given 400 cGy of γ-irradiation as were the wild type controls (FIG. 9B). All wild type mice survived. However, all irradiated Ku70$^{-/-}$ mice died within two weeks.

Gastrointestinal Abnormalities in Ku70$^{-/-}$ Mice

Figure 10A:
FIG. 10 Histological appearance of segmental gastrointestinal abnormalities of Ku70$^{-/-}$ mice. Gastrointestinal tissues from a three-month-old Ku70$^{-/-}$ mouse were stained with hematoxylin and eosin and photographed. (A) Normal appearance of the intestine showing the presence of ganglions (400×). (B) Section of intestine from the same animal showing absence of ganglion neurons (400×). (C) At a lower magnification (100×) segmental aganglionosis that developed in a Ku70$^{-/-}$ mouse is demonstrated. The left portion of the specimen shows complete absence of ganglion neurons. This phenotype is associated with the effacement of the typical morphology of the intestinal villi, dilation of intestinal lumen, and denudation of the mucosa, as well as segmental distention of the intestine. In contrast, the right portion of the specimen shows a normal appearance as observed in the wild-type littermates.
Figure 10B:
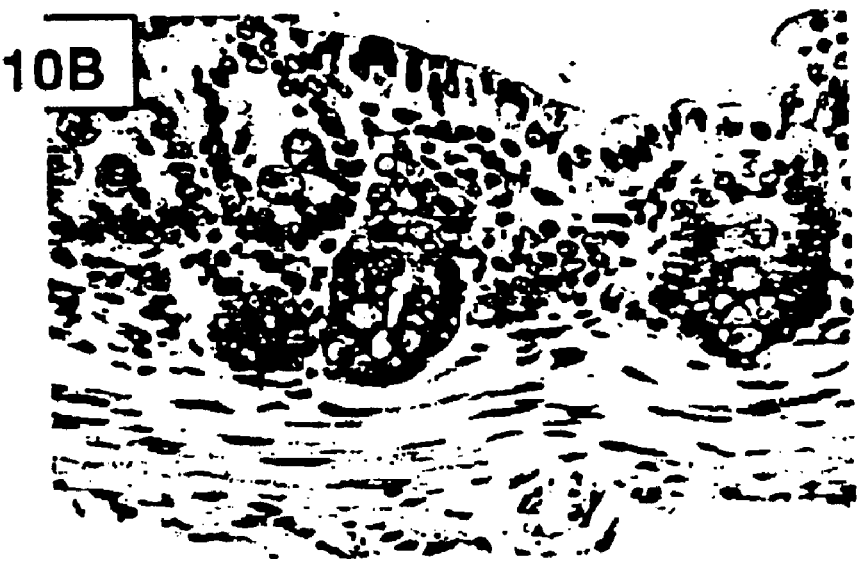
Figure 10C:

In our experimental group of Ku70$^{-/-}$ mice, we observed that 14.2% died without evidence of lymphoma. Histological examination showed that all these mice, as well as 60% of the lymphoma-bearing Ku70$^{-/-}$ mice, showed unique gastrointestinal abnormalities. Mild to severe segmental aganglionosis was observed, affecting the small intestine and the colon (FIG. 10). This phenotype was associated with the effacement of the typical morphology of the intestinal villi, dilatation of intestinal lumens and denudation of the intestinal mucosa, causing functional obstruction and progressive distention of the intestine. In some cases, we observed this alteration even in the esophagus and stomach. These changes were similar to those described in Hirschsprung disease (Badner, et al., 1990). Death caused by the more severe form of this phenotype began around 5 weeks of age and peaked around 12 weeks, much earlier than the onset of lymphoma death at 14 weeks. These abnormalities were not observed in heterozygous and wild type mice up to 8 months of age.

Ku70 Expression is Altered in Human T-cell Lymphomas

Figure 11A:
FIG. 11 Ku70 alteration in human tumors. Immunohistochemical analysis of Ku70 expression in human T-cell lymphomas. (A-C), B-cell lymphomas (D-F) and in human normal spleen (G). The photomicrograph of the spleen (paraffin) illustrates the nuclear staining against Ku70 (G). (A) Photomicrograph illustrating a T-cell lymphoma (sample #T2—paraffin) with positive nuclear staining against Ku70, (B and C) Photomicrographs of T-cell lymphomas (samples #T13 and T9—paraffin and frozen, respectively) showing negative immunohistochemical staining against Ku70. In panel (C), the arrows point to endothelial cells with positive nuclear staining for Ku70, which served as internal positive controls. (D) Photomicrograph illustrating a B-cell lymphoma (sample #B4—paraffin) with positive nuclear staining against Ku70. (E) Photomicrograph of a B-cell lymphoma (sample #B8—paraffin) showing negative immunohistochemical staining against Ku70. (F) Photomicrograph of a B-cell lymphoma (sample #B9—frozen) showing cytoplasmic staining of Ku70. Original magnification: A to G, 400×. (H) Representative PCR-SSCP analysis. Lane 3 illustrates the Ku70 band shift identified by PCR-SSCP corresponding to sample #T3. Lane 1, internal control (normal); lane 2, tumor corresponding to sample #T8, showing no band shift. Direct sequencing results of the PCR product obtained from tumor sample #T3 are shown below. The single base pair substitution (ACA→ATA) was found to be tumor-specific (absent in normal tissue) affecting codon 292, changing a threonine to isoleucine. (I) Representative RT-PCR direct sequencing from a T-cell lymphoma (sample #T3) and its corresponding normal tissue. Single base substitutions are indicated at codons 452 (ATC→GTC) and 453 (ATG→ACG), changing isoleucine to valine and methionine to threonine, respectively. These alterations were found to be tumor-specific and were absent in normal tissue. (J) Representative RT-PCR direct sequencing from a neuroblastoma (sample #N10) and its corresponding normal tissue. Single base substitutions are indicated at codon 530 (TAC→CAC) and codon 529 (GTT→GTC), changing tyrosine to histidine at codon 530, and producing a silent mutation at codon 529 (valine to valine), respectively. These mutations were also found to be tumor-specific and were absent in corresponding normal tissue.
Figure 11B:
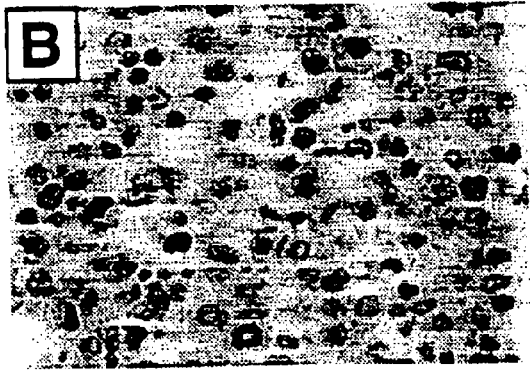
Figure 11C:
Figure 11D:

Because of the high incidence of T-cell lymphomas in Ku70$^{-/-}$ mice, we evaluated the possibility that abnormal expression of Ku70 also occurs in human T-cell lymphomas. Seven patients with T-cell lymphomas, classified by a panel of antibodies to specific cell surface markers and molecular probes, were analyzed. Immunohistochemical studies using a purified rabbit antiserum specific to Ku70, showed an intense nuclear staining pattern of Ku70 protein in human normal lymphocytes of lymph nodes (FIG. 11A) and spleen samples. However, four of the seven T-cell lymphomas analyzed showed undetectable Ku70 levels (FIG. 11C), while the remaining 3 cases displayed normal nuclear immunoreactivities (FIG. 11B). In the four Ku70-negative cases, inflammatory cellular infiltrates in the periphery of the tumor were found to have a strong nuclear staining, serving as internal positive controls.

Figure 11E:
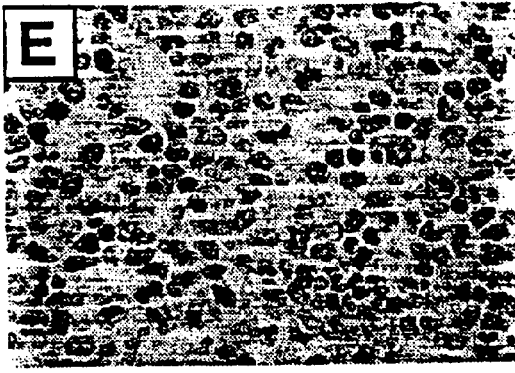
Figure 11F:
Figure 11G:
Figures 1, 11H:
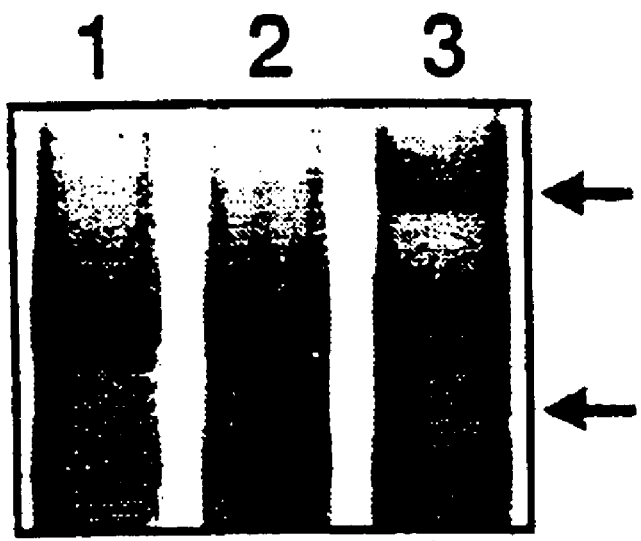
Figures 2, 11H:
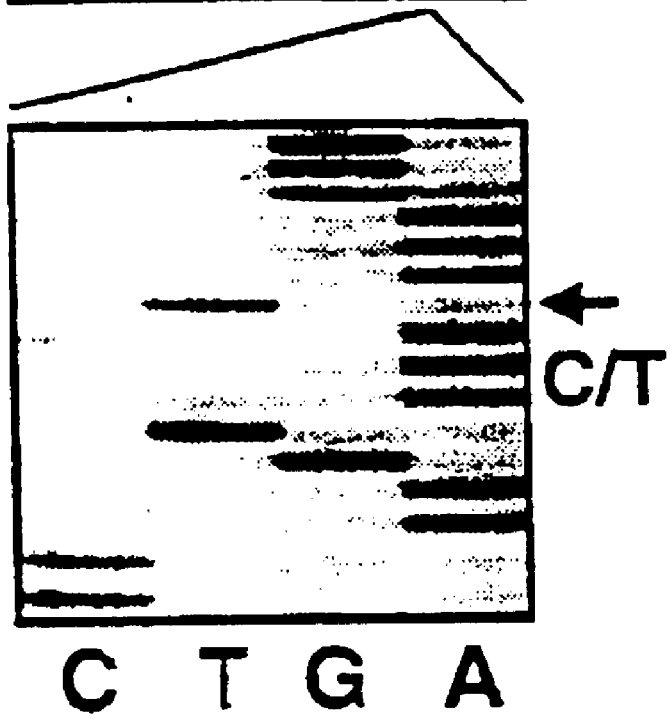
Figures 11I, 11J:
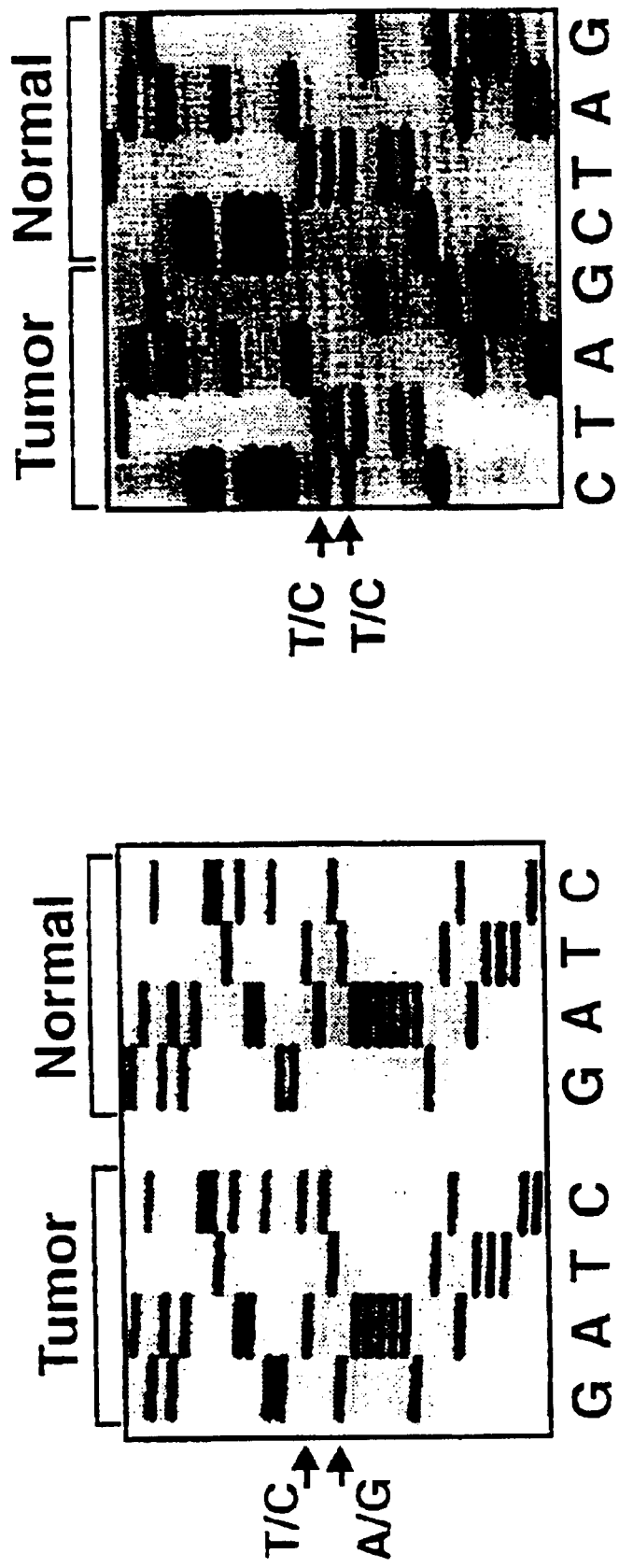
Figure 12A:
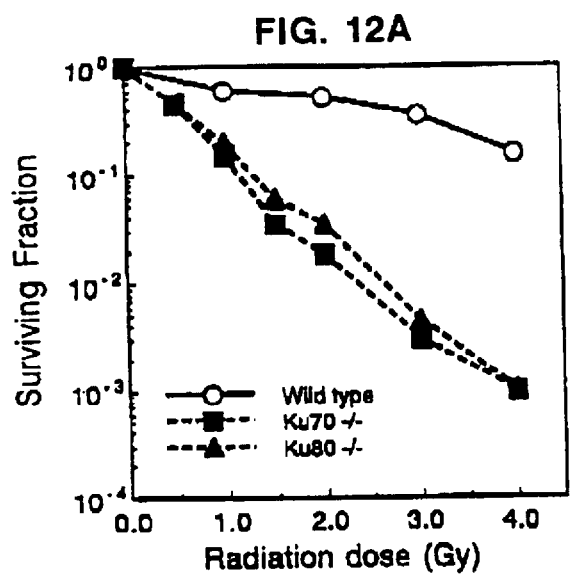
FIG. 12 Effect of (A) radiation, (B) bleomycin, (C) Adriamycin, and (D) Etoposide on Ku70 and Ku80 deficient mouse cells.
Figure 12B:
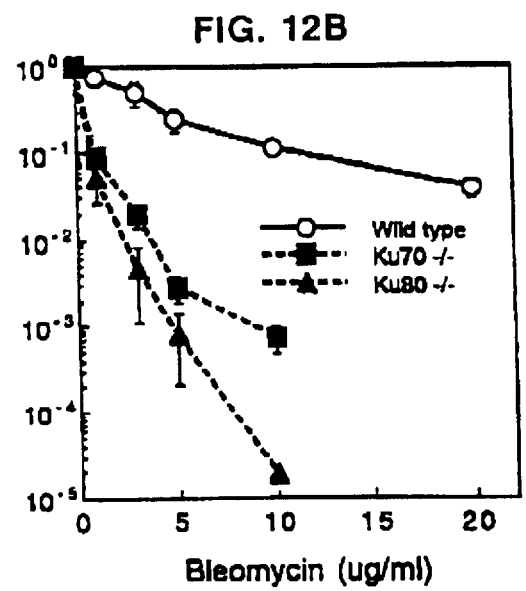
Figure 12C:
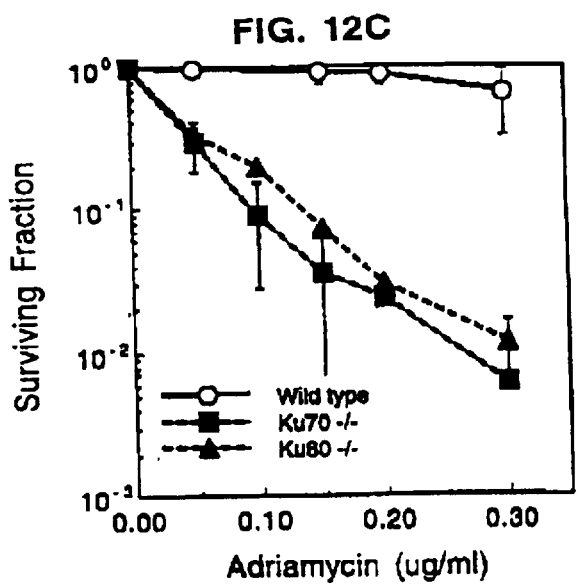
Figure 12D:
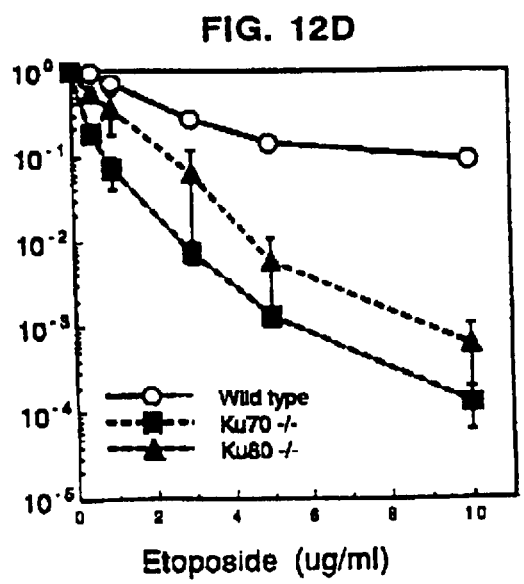

We also analyzed the expression status of p53 in these seven tumors. Of the four Ku70-negative T-cell lymphomas, three cases had a normal, undetectable level of p53 (FIG. 11F) and only one case displayed a mutated p53 phenotype. The remaining three T-cell lymphoma cases, which had a normal Ku70 expression (FIG. 11B), showed a mutated p53 phenotype (FIG. 11E).

Experimental Discussion

The present study reveals a novel characteristic of the Ku70$^{-/-}$ phenotype, the propensity for malignant transformation, both in vitro and in vivo. In vitro, this is expressed in terms of increased rate of sister chromatid exchange, frequent spontaneous neoplastic transformation of primary fibroblasts and anchorage-independent growth of the transformed foci in soft agar. In vivo, Ku70$^{-/-}$ mice spontaneously develop thymic and disseminated T-cell lymphomas, although the p53 phenotype in these tumors was normal. Concordant with these data, tumor specimens from human T-cell lymphomas also showed a pathological lack of Ku70 protein. These findings directly demonstrate that inactivation of the Ku70 gene facilitates neoplastic growth, and strongly suggest the Ku70 locus as a candidate tumor suppressor gene for murine and human T-cell lymphoma.

The specificity of the Ku70$^{-/-}$ phenotype for the development of T-cell but not B-cell lymphoma is consistent with our recent observation that the development of B-lymphocytes was absent in Ku70$^{-/-}$ mice (Ouyang, et al., 1997). In contrast to SCID and Ku80$^{-/-}$ mice, in which both T- and B-lymphocyte development is arrested at early progenitor stages (Bosma and Carroll, 1991, Carroll and Bosma, 1991, Carroll, et al., 1989, Lieber, et al., 1988, Nussenzweig, et al., 1996, Zhu, et al., 1996), the absence of Ku70 blocks neither TCR gene rearrangement nor the development of mature T cells (Gu, et al., 1997, Ouyang, et al., 1997). Nonetheless, the T-cell specific differentiation was suboptimal in Ku70$^{-/-}$ mice, with a 50- to 100-fold fewer thymocytes compared to the wild type littermates. These results suggest that there may be an alternate or residual, and Ku70$^{-/-}$ independent pathway for TCR V(D)J recombination and maturation of T-cells, although it may be less efficient, or does not provide all the necessary signals to fully effect the developmental transition. Another possible explanation for the lack of expansion of Ku70$^{-/-}$ DP thymocytes may be associated with the intrinsic propensity of DP cells to undergo apoptosis (Smith, et al., 1989), which may be further enhanced by the absence of Ku70. Consistent with this paradigm, we found that SV40-transfected Ku70$^{-/-}$ cells were extremely susceptible to radiation-induced apoptosis relative to wild type controls.

The mechanism for the induction of thymic lymphoma in Ku70$^{-/-}$ mice is not clear at present. It is reasonable to hypothesize that a thymocyte maturation defect and thymic malignancies are mechanistically related, and associated with abnormalities in DNA DSB repair, a characteristic of the Ku70$^{-/-}$ cells. Although residual DSB rejoining may be responsible for the apparent TCR V(D)J recombination, alternative DNA repair pathways may exist in the absence of Ku70. Such pathways may functionally complement the Ku70 gene and participate in TCR gene rearrangement. On the other hand, the rescue of TCR gene rearrangement and T-cell proliferation in a global DNA repair-deficient environment may result in unscheduled gene translocations, leading to the development of T-cell malignancies. Consistent with this model is our current observation on the increased frequency of neoplastic transformation in Ku70$^{-/-}$ fibroblasts, suggesting that loss of Ku70 may constitute one critical event in the multistep transformation processes.

The hypothesized link between deficient DSB repair, defective T-cell differentiation and tumor development in Ku70$^{-/-}$ mice is consistent with the experimental results obtained in irradiated SCID mice (Danska, et al., 1994). While SCID cells were shown to be deficient in the repair of radiation-induced DSB and V(D)J recombination (Bosma and Carroll, 1991, Carroll and Bosma, 1991, Carroll, et al., 1989, Lieber, et al., 1988), treatment of newborn SCID mice with a sublethal radiation dose of 100 cGy restored normal T-cell receptor TCRβ recombination, T-cell maturation and thymocyte proliferation, but not IgM rearrangement or B-cell development (Danska, et al., 1994). Relevant to this study is the observation that all of the irradiated SCID mice eventually developed T-cell tumors, but not tumors of B-lymphoid or non-lymphoid origin. These data support the notion that the induction of alternative pathways for DSB rejoining, apparently activated by radiation, can restore TCR V(D)J recombination, but because of their deficiency in DSB repair, these activities promote the malignant transformation of T-cells. Therefore, the T-lineage specificity of neoplastic transformation, either induced by low-dose irradiation (as in the case of SCID mice) or occurring spontaneously (as in Ku70$^{-/-}$ mice), may reflect an association between defective DNA DSB repair and TCR gene rearrangement.

Although Ku70$^{-/-}$ cells of non-lymphoid lineage, such as primary fibroblasts, can undergo spontaneous transformation in vitro, we observed no spontaneous tumors other than T-cell lymphomas in the Ku70$^{-/-}$ mice. This may be due to the fact that nearly all animals observed up to the age of 8 months died of either T-cell lymphoma or a Hirschsprung-like gastrointestinal syndrome. Mild to severe segmental aganglionosis in the gastrointestinal tract was, in fact, detected in the great majority of Ku70$^{-/-}$ mice examined by autopsy. This unexpected phenotype was associated with the effacement of the typical morphology of the intestinal villi, dilatation of the intestinal lumens and denudation of the intestinal mucosa, disorders similar to those described in the Hirschsprung disease (HSCR). Human HSCR is a congenital disorder of the enteric nervous system characterized by the absence of enteric ganglia (Badner, et al., 1990, Pingault, et al., 1997). Three genes for HSCR have been identified, including the RET proto-oncogene (Angrist, et al., 1995, Attie, et al., 1995), the gene encoding the endothelin B receptor (EDNRB) (Amiel, et al., 1996), and the endothelin 3 gene (EDN3) (Edery, et al., 1996, Hofstra, et al., 1996). In mice, spontaneous and in vitro-induced mutations affecting the RET, EDNRB, and EDN3 genes generate phenotypes similar to human HSCR. Another murine model of HSCR disease is the Dominant megacolon (Dom), a spontaneous mouse mutation in which the target gene has not yet been identified (Pavan, et al., 1995, Pingault, et al., 1997). Interestingly, the Dom mutation has been mapped to the middle-terminal region of mouse chromosome 15. Using known polymorphisms for conserved human/mouse genes, the homology between the Dom locus and human chromosome 22q12-q13 has been established (Pingault, et al., 1997). Although the mouse Ku70 locus is also mapped to chromosome 15 (Takiguchi, et al., 1996), it is unlikely that the Dom gene is disrupted in the Ku70$^{-/-}$ mice, because of the fact that the homozygous Dom mutation results in a lethal phenotype. As the Dom gene sequences become available, it would be of great interest to examine whether the expression of Dom gene, or that of the other HSCR genes, are affected by the absence of Ku70 protein.

The spontaneous development of T-cell tumors in the Ku70$^{-/-}$ mice constitutes a major difference from the Ku80$^{-/-}$ and SCID phenotypes. It is, however, compatible with the thymic lymphoblastic lymphomas reported in Atm-deficient mice (Barlow, et al., 1996), the predisposition to lymphoreticular malignancies in ataxia telangiectasia patients (Boder, 1975, Sedgewick and Boder, 1991), and the development of thymic lymphoblastic lymphoma recently reported in DNA-PKcs null mice (Jhappan, et al., 1997). However, AT mutations are associated with other tumor types as well. Targeted disruption of one of the prototype tumor suppressors, the p53 gene, also leads to the development of thymic tumors in mice (Donehower, et al., 1992, Jacks, et al., 1994, Purdie, et al., 1994, Tsukada, et al., 1993). However, a dramatic susceptibility to the development of other neoplasms, such as sarcomas, was also observed in p53$^{-/-}$ mice (Donehower, et al., 1992, Jacks, et al., 1994).

The dominance of T-cell tumors in Ku70$^{-/-}$ mice is unique, especially in view of their normal p53 phenotype. Our analysis of human tumor biopsies, however, suggests a possible association between Ku70 and p53 in suppressing human T-cell lymphoma. We observed that 3 out of 7 human T-cell lymphomas lacked Ku70 expression while showing a wild type p53 phenotype, another three had the converse pattern with normal Ku70 and abnormal p53 expression, and one tumor exhibited abnormal expression of both genes. The lack of altered p53 expression in the Ku70$^{-/-}$ murine lymphomas, and the association of the human T-cell lymphoma phenotypes with abnormalities in either Ku70 and/or p53 suggest that they may serve in overlapping pathways of T-cell tumor suppression.

In summary, our studies show that inactivation of Ku70 results in a distinct phenotype, relative to Ku80$^{-/-}$ and SCID mice, which are deficient in the other component of the DNA-PK complex. Consistent with the observation that the Ku70$^{-/-}$ mouse is highly susceptible to the development of spontaneous thymic and disseminated T-cell lymphoma, most of the human T-cell lymphomas examined also showed a lack of Ku70 expression. Collectively, our studies directly demonstrate that the disruption of Ku70 facilitates neoplastic growth and strongly suggest that the Ku70 locus as a candidate tumor suppressor gene for murine and human T-cell lymphoma. Although the Ku70$^{-/-}$ rodent model did not exhibit other types of tumor, the high frequency of sister chromatid exchanges in Ku70$^{-/-}$ fibroblasts and their high susceptibility to spontaneous neoplastic transformation raises the possibility that other human tumors may also be affected by the function of the Ku70 locus. Further experiments will be required to assess this possibility.

Experimental Procedures

Target Disruption of Ku70 and Generation of Ku70$^{-/-}$ Mice

Mouse genomic Ku70 gene was isolated from a sCos-I cosmid library constructed from a mouse strain 129 embryonic stem cell line (Takiguchi, et al., 1996). The replacement vector was constructed using a 1.5 kb 5'-fragment which contains the promoter locus with four GC-box and exon 1, and a 8 kb EcoRV-EcoRI fragment extending from intron 2 to intron 5 as indicated in FIG. 1a. Homologous replacement results in a deletion of 336-bp exon 2 including the translational initiation codon.

The targeting vector was linearized with Not 1 and transfected into CJ7 embryonic stem (ES) cells by electroporation using a Bio-Rad Gene Pulser. Three hundred ES cell clones were screened, and 5 clones carrying the mutation in Ku70 were identified by Southern blotting. Positive ES clones were injected separately into C57BL/6 blastocysts to generate chimeric mice. One clone was successfully transmitted through the germline after chimeras were crossed with C57 BL/6 females. Homozygous Ku70$^{-/-}$ mice were generated by intercrossing Ku70$^{+/-}$ heterozygotes.

The genotypes of the mice were first determined by tail PCR analysis which distinguishes endogenous from the targeted Ku70 allele, and subsequently confirmed by Southern blot analysis. The PCR reaction contained 1 µg genomic DNA; 0.6 µM (each) of primers HO-2: GGGCCAGCTCATTCCTCCACTCATG, HO-3: CCTACAGTGTACCCGGACCTATGCC and HO-4: CGGAACAGGACTGGTGGTTGAGCC; 0.2 mM (each) dNTP; 1.5 mM MgCl$_2$ and 2.5 U of Taq polymerase. Cycling conditions were 94° C. for 1 min, 64° C. for 1 min, 72° C. for 1 min (30 cycles), followed by an extension at 72° C. for 10 min. Primers HO-2 and HO-4 give a product of the targeted allele that is ~380 bp; primers HO-3 and HO-4 yield a wild type product of 407 bp.

Cell Cultures and Determination of Radiosensitivity

Monolayers of cells (1–2×10$^5$ cells) were seeded in 60 mm petri dishes and cultured at 37° C. for 3 days at which time they were near confluence (1–2×10$^6$ cells per dish). The culture medium was then changed daily, and the cells were at a density-inhibited plateau phase by day 6. The pulse-labeling index, as determined by incubation for 30 min with 10 µCi/ml of $^3$H-thymidine and autoradiographic analysis, was <1% indicating a paucity of cycling cells. Experiments were performed on day 6 or 7.

Survival curves were obtained by measuring the colony-forming ability of irradiated cells as described previously (Nagasawa, et al., 1991). A colony containing more than 50 cells was scored as a survivor. Cell survival was always normalized to the cloning efficiency of untreated controls. All experiments were performed at least three times and yielded consistent results.

Spontaneous Transformation of Ku70-Deficient Cells

To study the spontaneous transformation of Ku70-deficient fibroblasts, the well established protocols of Little were used (Little, 1979). Cells were seeded into 6 replicate 100-mm plastic Falcon petri dishes, at densities designed to yield approximately 4000 to 7000 viable (colony forming) cells per dish. After a 3- to 4-week incubation at 37° C., with twice weekly renewal of the nutrient medium, the cultures were fixed with 95% ethanol and stained with 0.1% crystal violet. Transformed foci (Type III) appeared as dense piled-up colonies of cells overlying the normal monolayer. Cells from these foci were isolated, expanded and further tested for their ability to grow in soft agar in an anchorage-independent manner.

In parallel with the above, three 100 mm dishes were seeded from a 1:50 dilution of the same cell suspension (80 to 140 viable cells) in each group in order to determine the actual colony forming efficiency. After a 10- to 12-day incubation at 37° C., the samples were fixed and stained, the number of viable colonies counted, and the cloning efficiency determined, which was then used to calculate the number of viable cells seeded in the transformation dishes. The transformation frequency was determined by dividing the total number of transformed foci scored in a treatment group by the total number of viable cells seeded, and it was therefore expressed as transformants per viable cell.

For colony formation in soft agar, a modified MacPherson method (MacPherson, 1973) was used (Nagasawa, et al., 1987). Plastic petri dishes (60 mm) were coated with a layer of 5 ml of 0.5% agarose in medium supplemented with 20% heat-inactivated fetal bovine serum. Two milliliters of the cell suspension were mixed with 4 ml of the 0.5% agarose solution; 1.5 ml of the resulting cell suspension were plated into the agarose-coated dishes. Subsequently, the cultures were fed once a week by adding 1 ml of complete medium (without agarose). The size of the colonies was monitored at 2 days, 1, 2, and 3 weeks after seeding by taking photomicrographs of the cultures on an inverted microscope.

Analysis of Sister Chromatid Exchange

For analysis of sister chromatid exchange (SCE), the protocols used by Nagasawa et al (Nagasawa, et al., 1991) were followed. Briefly, cells were subcultured from density-inhibited cultures into three replicate T-25 tissue culture flasks in fresh complete medium containing 10$^{-5}$ M bromodeoxyuridine (BrdUrd) for two rounds of cell replication. For three successive 4-h intervals beginning 15 h after subculturing, colcemid (0.2 g/ml) was added to one of the flasks for a 4-h interval prior to fixation. Therefore, harvesting was carried out over a total period of 12 h. Chromosomes were prepared for the analysis of SCE by the air-dry method, as previously described (Nagasawa and Little, 1979, Nagasawa, et al., 1991). The differential staining of sister chromatids was carried out by the fluorescence plus Giemsa technique (Nagasawa, et al., 1991, Perry and Wolff, 1974). SCE was analyzed at peak mitotic indices after completion of the first or second mitosis.

Immunohistochemistry

Normal and tumor tissue samples from wild type and/or Ku70$^{-/-}$ mice were fixed in either 10 buffered formalin and embedded in paraffin, or embedded in OCT compound (Miles Laboratories) and frozen in liquid nitrogen at −70° C. Seven human T-cell lymphomas were analyzed, as well as human normal tissue samples of lymph node, spleen, and colon. Sections (5 µm) were stained with hematoxylin and eosin, and representative samples were selected for immunohistochemical analysis. Immunophenotyping was performed using an avidin-biotin immunoperoxidase technique (Cordon-Cardo and Richon, 1994, Serrano, et al., 1996). Primary antibodies included anti-mouse CD45 (purified rat monoclonal antibody, 1:500, PharMingen), anti-mouse CD3 (purified rabbit serum, 1:1000, Dako), anti-mouse B220 (purified rat monoclonal antibody, 1:1000, PharMingen), and anti-mouse CD19 (purified rat monoclonal antibody, 1:1000, PharMingen), and were incubated overnight at 4° C. We also used a purified rabbit antiserum to the Ku70 nuclear protein (1:500 dilution), and a purified sheep antiserum that recognizes murine p53 (Calbiochem, 1:1000). Samples were subsequently incubated with biotinylated secondary antibodies (Vector Laboratories) for 30 min (goat anti-rabbit, 1:500; rabbit anti-rat, 1:100; rabbit anti-sheep, 1:400), and then with avidin-biotin peroxidase complexes (1:25 dilution, Vector Laboratories) for 30 min. Diaminobenzadine was used as the chromogen and hematoxylin as the counter stain. Wild type lymphoid organs including thymus, spleen and lymph nodes from different mice were used for titration of the antibodies and positive controls. For negative controls, primary antibodies were substituted with class-matched but unrelated antibodies at the same final working dilutions (Ouyang, et al., 1997).

Flow Cytometry Analysis of the Spontaneous Tumors

Cell lines were established from each primary tumor as follows. Samples of the tumors were dispersed into cell suspension and plated at various densities in RPMI supplemented with 10% heat-inactivated fetal bovine serum and antibiotics. The cell cultures were split 1:2 and 1:4 until they become established.

For flow cytometry analysis, tumor cells of early passages were stained with combinations of antibodies specific for various T- and B-lymphocyte surface markers, such as PE-labeled anti-mouse CD4, and FITC-labeled anti-mouse CD8, and analyzed on a Becton Dickinson FAC scan with Cell Quest software (Ouyang, et al., 1997).

References for the Second Series of Experiments
1. Amiel, J., T. Attie, D. Jan, A. Pelet, P. Edery, C. Bidaud, D. Lacombe, P. Tam, J. Simeoni, E. Flori, C. Nihoul-Fekete, A. Munnich and S. Lyonnet (1996) Heterzygous endothelin receptor B (EDNRB) mutations in isolated Hirschsprung disease. Hum. Mol. Genet., 5, 355–367.
2. Anderson, C. W. (1993) DNA damage and the DNA-activated protein kinase. Trends Biochem. Sci., 18, 433–437.
3. Angrist, M., S. Bolk, B. Thiel, E. G. Puffenberger, R. M. W. Hofstra, C. H. C. M. Buys, D. T. Cass and A. Chakravarti (1995) Mutation analysis of the RET receptor tyrosine kinase in Hirschsprung disease. Hum. Mol. Genet., 4, 821–830.
4. Attie, T., A. Pelet, P. Edery, C. Eng, J. M. Mulligan, J. Amiel, L. Boutrand, C. Beldjord, C. Niboul-Fekete, A. Munnich, B. Ponder and S. Lyonnet (1995) Diversity of RET proto-oncogene mutations in familial and sporadic Hirschsprung disease. Hum. Mol. Genet., 4, 1381–1386.
5. Badner, J. A., W. K. Sieber, K. L. Garver and A. Chakravati (1990) A genetic study of Hirschsprung disease. Am. J. Hum. Genet., 46, 568–580.
6. Barlow, C., S. Hirotsune, R. Paylor, M. Liyanage, M. Eckhaus, F. Collins, Y. Shiloh, J. N. Crawley, T. Ried, D. Tagle and A. Wynshaw-Boris (1996) Atm-deficient mice: a paradigm of Ataxia telangiectasia. Cell, 86, 159–171.
7. Biedermann, K. A., J. R. Sun, A. J. Giaccia, L. M. Tosto and J. M. Brown (1991) scid mutation in mice confers hypersensitivity to ionizing radiation and a deficiency in DNA double-strand break repair. Proc. Natl. Acad. Sci. USA, 88, 1394–1397.
8. Blunt, T., N. J. Finnie, G. E. Taccioli, G. C. M. Smith, J. Demengeot, T. M. Gottlieb, R. Mizuta, A. J. Varghese, F. W. Alt, P. A. Jeggo and S. P. Jackson (1995) Defective DNA-dependent protein kinase activity is linked to V(D)J recombination and DNA repair defects associated with the murine scid mutation. Cell, 80, 813–823.
9. Boder, E. (1975) Ataxia-telangiectasia: some historic, clinical and pathologic observations. Birth Defects, 11, 255–270.
10. Bosma, G. C., R. P. Custer and M. J. Bosma (1983) A severe combined immunodeficiency mutation in the mouse. Nature (London), 301, 527–530.
11. Bosma, M. J. and A. M. Carroll (1991) The SCID mouse mutant: definition, characterization, and potential uses. Annu. Rev. Immunol., 9, 323–350.
12. Cai, Q.-Q., A. Plet, J. Imbert, M. Lafage-Pochitaloff, C. Cerdan and J.-M. Blanchard (1994) Chromosomal location and expression of the genes coding for Ku p70 and p80 in human cell lines and normal tissues. Cytogenet Cell Genet, 65, 221–227.
13. Carroll, A. M. and M. J. Bosma (1991) T-lymphocyte development in scid mice is arrested shortly after the initiation of T-cell receptor δ gene recombination. Genes Dev., 5, 1357–1366.
14. Carroll, A. M., R. R. Hardy and M. J. Bosma (1989) Occurrence of mature B (IgM+, B220+) and T (CD3+) lymphocytes in scid mice. J. Immunol., 143, 1087–1093.
15. Chan, D. W. and S. P. Lees-Miller (1996) The DNA-dependent protein kinase is inactivated by autophosphorylation of the catalytic subunit. J. Biol. Chem., 271, 8936–8941.
16. Cleary, M. L. (1991) Oncogenic conversion of transcription factors by chromosomal translocations. Cell, 66, 619–622.
17. Cordon-Cardo, C., D. Dalbagni, G. T. Saez, M. R. Oliva, Z.-F. Zhang, J. Rosia, V. W. Reuter and A. Pellicer (1994) TP53 mutations in human bladder cancer: Genotype versus phenotypic patterns. Int. J. Cancer, 56, 347–353.
18. Cordon-Cardo, C. and V. M. Richon (1994) Expression of the retinoblastoma protein is regulated in normal human tissues. Am. J. Path., 144, 500–510.
19. Danska, J. S., F. Pflumio, C. J. Williams, O. Huner, J. E. Dick and C. J. Guidos (1994) Rescue of T cell-specific V(D)J recombination in SCID mice by DNA-damaging agents. Science, 266, 450–455.
20. Donehower, L. A., M. Harvey, B. L. Slagle, M. J. McArthur, C. A. Montgomery Jr., J. S. Butel and A. Bradley (1992) Mice deficient for p53 are developmentally normal but susceptible to spontaneous tumours. Nature (London), 356, 215–221.
21. Dvir, A., S. R. Peterson, M. W. Knuth, H. Lu and W. S. Dynan (1992) Ku autoantigen is the regulatory component of a template-associated protein kinase that phosphorylates RNA polymerase II. Proc. Natl. Acad. Sci. USA, 89, 11920–11924.
22. Edery, P., T. Attie, J. Amiel, A. Pelet, C. Eng, R. M. W. Hofstra, H. Martelli, C. Bidaud, A. Munnich and S. Lyonnet (1996) Mutation of the endothelin-3 gene in the Waardenburg-Hirschsprung disease (Shah-Waardenburg syndrome). Nature Genet., 12, 442–444.
23. Gottlieb, T. M. and S. P. Jackson (1993) The DNA-dependent protein kinase: requirement for DNA ends and association with Ku antigen. Cell, 72, 131–142.
24. Gu, Y., K. J. Seidl, G. A. Rathbun, C. Zhu, J. P. Manis, N. van der Stope, L. Davidson, H. -L. Cheng, J. M. Sekiguchi, K. Frank, P. Stanhope-Baker, M. S. Schlissel, D. B. Roth and F. W. Alt (1997) Growth retardation and leaky SCID phenotype of Ku70-deficient mice. Immunity, 7, 653–665.
25. Hofstra, R. M. W., J. Oningu, G. Tan-Sindhunata, Y. Wu, E.-J. Kamsteeg, R. P. Stulp, C. van Ravenswaaij-Arts, D. Majoor-Krakauer, M. Angrist, A. Chakravarti, C. Maijeers and C. H. C. M. Buys (1996) A homozygous mutations in the endothelin-3 gene associated with a combined Waardenburg type 2 and Hirschsprung phenotype (Shah-Waardenburg syndrome). Nature Genet., 12, 445–447.
26. Jacks, T., L. Remington, B. O. Williams, E. M. Schmitt, S. Halachmi, R. T. Bronson and R. A. Weinberg (1994) Tumor spectrum analysis in p53-mutant mice. Curr. Biol., 4, 1–7.
27. Jackson, S. P. and P. A. Jeggo (1995) DNA double-strand break repair and V(D)J recombination, involvement of DNA-PK. Trends Biochem. Sci., 20, 412–415.
28. Jeggo, P. A., G. E. Taccioli and S. P. Jackson (1995) Menage a trois: double strand break repair, V(D)J recombination and DNA-PK. BioEssays, 17, 949–957.
29. Jhappan, C., H. C. Morse III, R. D. Fleischmann, M. M. Gottesman and G. Merlino (1997) DNA-PKcs: a T-cell tumour suppressor encoded at the mouse scid locus. Nature Genet., 17, 483–486.
30. Kaplan, E. L. and P. Meier (1958) Nonparametric estimation from incomplete observations. J. Am. Stat. Assoc., 53, 457–481.
31. Kirchgessner, C. U., C. K. Patil, J. W. Evans, C. A. Cuomo, L. M. Fried, T. Carter, M. A. Oettinger and J. M. Brown (1995) DNA-dependent kinase (p350) as a candidate gene for the murine SCID defect. Science, 267, 1178–1183.
32. Lees-Miller, S. P. (1996) The DNA-dependent protein kinase, DNA-PK: 10 years and no ends in sight. Biochem. Cell Biol., 74, 503–512.
33. Lees-Miller, S. P., R. Godbout, D. W. Chan, M. Weinfeld, R. S. Day III, G. M. Barron and J. Allalunis- Turner (1995) Absence of p350 subunit of DNA-activated protein kinase from a radiosensitive human cell line. Science, 267, 1183–1185.
34. Levine, A. J. (1997) p53, the cellular gatekeeper for growth and division. Cell, 88, 323–331.
35. Liang, F. and M. Jasin (1996) Ku80-deficient cells exhibit excess degradation of extrachromosomal DNA. J. Biol. Chem., 271, 14405–14411.
36. Lieber, M. R., J. E. Hesse, S. Lewis, G. C. Bosma, N. Rosenberg, K. Mizuuchi, M. J. Bosma and M. Gellert (1988) The defect in murine severe combined immune deficiency: joining of signal sequences but not coding segments in V(D)J recombination. Cell, 55, 7–16.
37. Little, J. B. (1979) Quantitative studies of radiation transformation with the A31–11 mouse BALB/3T3 cell line. Cancer Res., 39, 1474–1480.
38. MacPherson, I. (1973) Soft agar techniques. In Tissue Culture Methods and Applications, P. F. Kruse Jr. eds. (New York: Academic Press, pp. 276–280.
39. Mimori, T., M. Akizuki, H. Yamagata, S. Inada, S. Yoshida and M. Homma (1981) Characterization of a high molecular weight acidic nuclear protein recognized by autoantibodies in sera from patients with polymyositis-scleroderma overlap. J. Clin. Invest., 68, 611–620.
40. Nagasawa, H. and J. B. Little (1979) Effect of tumor promoters, protease inhibitors and repair processes on x-ray-induced sister chromatid exchanges in mouse cells. Proc. Natl. Acad. Sci. USA, 76, 1943–1947.
41. Nagasawa, H., J. B. Little, W. C. Inkret, S. Carpenter, M.-R. Raju, D. J. Chen and G. F. Strniste (1991) Response of x-ray sensitive CHO mutant cells (xrs-6c) to radiation. II. Relationship between cell survival and the induction of chromosomal damage with low doses of α particles. Radiat. Res., 126, 280–288.
42. Nagasawa, H., G. B. Zamansky, E. F. McCone, C. M. Arundel, E. Matkin and J. B. Little (1987) Spontaneous transformation to anchorage-independent growth of a xeroderma pigmentosum fibroblast cell strain. Journal of Investigative Dermatology, 88, 149–153.
43. Nussenzweig, A., C. Chen, V. da Costa Soares, M. Sanchez, K. Sokol, M. C. Nussenzweig and G. C. Li (1996) Requirement for Ku80 in growth and immunoglobulin V(D)J recombination. Nature (London), 382, 551–555.
44. Ouyang, H., A. Nussenzweig, A. Kurimasa, V. da Costa Soares, X. Li, C. Cordon-Cardo, W. Li, N. Cheong, M. Nussenzweig, G. Iliakis, D. Chen and G. C. Li (1997) Ku70 is required for DNA repair but not for TCR gene recombination in vivo. J. Exp. Med., 186, 921–929.
45. Pan, Z. Q., A. A. Amin, E. Gibbs, H. Niu and J. Hurwitz (1994) Phosphorylation of the p34 subunit of human single-stranded-DNA-binding protein in cyclin A-activated G1 extracts is catalyzed by cdk-cyclin A complex and DNA-dependent protein kinase. Proc. Natl. Acad. Sci. USA, 91, 8343–8347.
46. Pavan, W. J., R. A. Liddell, A. Wright, G. Thibaudeau, P. G. Matteson, K. M. McHugh and L. D. Siracusa (1995) A high-resolution linkage map of the lethal spotting locus: a mouse model for Hirschsprung disease. Mammalian Genome, 6, 1–7.
47. Perry, P. and S. Wolff (1974) New giemsa method for the differential staining of sister chromatids. Nature (London), 251, 156–158.
48. Peterson, S. R., A. Kurimasa, M. Oshimura, W. S. Dynan, E. M. Bradbury and D. J. Chen (1995) Loss of the catalytic subunit of the DNA-dependent protein kinase in DNA double-strand-break-repair mutant mammalian cells. Proc. Natl. Acad. Sci. USA, 92, 3171–3174.
49. Pingault, V., A. Puliti, M. O. Prehu, A. Samadi, N. Bondurand and M. Goossens (1997) Human homology and candidate genes for the Dominant megacolon locus, a mouse model for Hirschsprung disease. Genomics, 39, 86–89.
50. Purdie, C. A., D. J. Harrison, A. Peter, L. Dobbie, S. White, S. E. Howie, D. M. Salter, C. C. Bird, A. H. Wylie, M. L. Hooper and A. R. Clarke (1994) Tumor incidence, spectrum and ploidy in mice with a large deletion in the p53 gene. Oncogene, 9, 603–609.
51. Rathmell, W. K. and G. Chu (1994) Involvement of the Ku autoantigen in the cellular response to DNA double-strand breaks. Proc. Natl. Acad. Sci. USA, 91, 7623–7627.
52. Roth, D. B., T. Lindahl and M. Gellert (1995) How to make ends meet. Curr. Biol., 5, 496–499.
53. Sedgewick, R. and E. Boder (1991) Ataxia-telangiectasia. In Handbook of Clinical Neurology, P. Vinken, G. Bruyn and H. Klawans eds. (New York: Elsevier Scientifice Publishers, pp. 347–423.
54. Serrano, M., H.-W. Lee, L. Chin, C. Cordon-Cardo, D. Beach and R. A. DePinho (1996) Role of the INK4a in tumor suppression and cell mortality. Cell, 85, 27–37.
55. Sipley, J. D., J. C. Menninger, K. O. Hartley, D. C. Ward, S. P. Jackson and C. W. Anderson (1995) Gene for the catalytic subunit of the human DNA-activated protein kinase maps to the site of the XRCC7 gene on chromosome 8. Proc. Natl. Acad. Sci. USA, 92, 7515–7519.
56. Smider, V., W. K. Rathmell, M. R. Lieber and G. Chu (1994) Restoration of x-ray resistance and V(D)J recombination in mutant cells by Ku cDNA. Science, 266, 288–291.
57. Smith, C. A., G. T. Williams, R. Kingston, E. J. Jenkinson and J. J. T. Owen (1989) Antibodies to CD3/T-cell receptor complex induce death by apoptosis in immature T cells in thymic cultures. Nature (London), 337, 181–184.
58. Suwa, A., M. Hirakata, Y. Takeda, S. A. Jesch, T. Mimori and J. A. Hardin (1994) DNA-dependent protein kinase (Ku protein-p350 complex) assembles on double-stranded DNA. Proc. Natl. Acad. Sci. USA, 91, 6904–6908.
59. Taccioli, G. E., T. M. Gottlieb, T. Blunt, A. Priestly, J. Demengeot, R. Mizuta, A. R. Lehmann, F. A. Alt, S. P. Jackson and P. A. Jeggo (1994) Ku80: product of the XRCC5 gene and its role in DNA repair and V(D)J recombination. Science, 265, 1442–1445.
60. Takiguchi, Y., A. Kurimasa, F. Chen, P. E. Pardington, T. Kuriyama, R. T. Okinaka, R. Moyzis and D. J. Chen (1996) Genomic structure and chromosomal assignment of the mouse Ku70 gene. Genomics, 35, 129–135.
61. Thompson, L. H. and P. A. Jeggo (1995) Nomenclature of human genes involved in ionizing radiation sensitivity. Mutat. Res., 337, 131–133.
62. Tsukada, T., Y. Tomooka, S. Takai, Y. Ueda, S. Nishikawa, T. Yagi, T. Tokunaga, N. Takeda, Y. Suda, S. Abe, I. Matsuo, Y. Ikawa and S. Aizawa (1993) Enhanced proliferative potential in culture of cells from p53-deficient mice. Oncogene, 8, 3313–3322.
63. Zhu, C., M. A. Bogue, D.-S. Lim, P. Hasty and D. B. Roth (1996) Ku86-deficient mice exhibit severe combined immunodeficiency and defective processing of V(D)J recombination intermediates. Cell, 86, 379–389.

Third Series of Experiments

Ku-Deficient Cells are Sensitive to γ-Rays and Chemotherapeutic Agents

Survival experiments using cells derived from either Ku70 or Ku80 knock-out mice have shown that these cells are very sensitive to γ-radiation and several chemotherapeutic agents, specifically those agents that induce DNA strand breaks, such as: bleomycin, etoposide, and adriamycin (FIG. 12).

HSP70 Promoter Analysis

Experiments were performed to test the transcriptional activity of the mouse hsp70 promoter. For these experiments, first, the plasmid N3Luc, a reporter gene construct which contains the mouse hsp70 promoter upstream of the firefly luciferase gene was used for our studies. Cells were transiently transfected with this mouse hsp70 promoter-driven luciferase reporter gene construct. Comparison of the luciferase activity before and 8 hours after heat shocking the cells demonstrated that a) this promoter showed little "leakiness"(i.e. low transcription under normal conditions) and b) a high heat-inducible activity. The transcriptional activity after a 15 minute 45° C. heat shock was at least 30 fold increased relative to control levels. Other investigators have reported even higher induction levels (>100 fold) for this promoter (Nguyen et al., J. Biol. Chem. 264: 10487 (1989)).

Mutant of the hsp70 promoter were then generated, including 5'-deletion, linkerscanner mutations and point mutations, fused to the firefly luciferase reporter gene (the mutant N3Luc construct is designated ΔN3Luc), and examined the heat-induced reporter gene expression. Our results showed that specific deletion (e.g., either at 5' or in the central region of hsp70 promoter) increased the heat induction of transcriptional activity (as measured by firefly luciferase reporter gene activity) by an additional several fold when compared to the heat inducibility of the intact, not mutated promoter. Further data indicate that in cells deficient in Ku70 or Ku80 the heat induction of hsp70 promoter activity is further enhanced.

Stable HeLa cells, containing human Ku70 cDNA or human Ku80 cDNA, in the antisense orientation, under the regulation of the Tet-Off™ expression system (Clonetech), were established. Upon induction of the expression system these cells should produce antisense Ku70 or Ku80 RNA, respectively. Experiments were performed showing (FIG. 13) that expression of either Ku70 or Ku80 antisense RNA increased the cytotoxic effect adriamycin by 3–5 fold at 1 μg/ml and that expression of Ku70 antisense RNA increased the cytotoxic effect of γ-radiation approximately 5 fold (at 6 Gy).

What is claimed is:

1. A method of screening for a compound that causes DNA damage, comprising:

a. contacting a Ku70$^{-/-}$ cell with the compound; and b. determining whether the compound causes DNA damage in the cell.

2. The method of claim 1, wherein the DNA damage is determined by measuring a reduction in cell survival.

* * * * *

SEQUENCE LISTING

<160> NUMBER OF SEQ ID NOS: 34

<210> SEQ ID NO 1
<211> LENGTH: 25
<212> TYPE: DNA
<213> ORGANISM: Mice

<400> SEQUENCE: 1
gggccagctc attcctccac tcatg                                          25

<210> SEQ ID NO 2
<211> LENGTH: 25
<212> TYPE: DNA
<213> ORGANISM: Mice

<400> SEQUENCE: 2
cctacagtgt acccggacct atgcc                                          25

<210> SEQ ID NO 3
<211> LENGTH: 24
<212> TYPE: DNA
<213> ORGANISM: Mice

<400> SEQUENCE: 3
cggaacagga ctggtggttg agcc                                           24

<210> SEQ ID NO 4
<211> LENGTH: 28
<212> TYPE: DNA
<213> ORGANISM: Mice

<400> SEQUENCE: 4
gggccaagaa tcttccagca gtttcggg                                       28

<210> SEQ ID NO 5
<211> LENGTH: 20
<212> TYPE: DNA
<213> ORGANISM: Mice

```
<400> SEQUENCE: 5
gaggaaaggt gacattgagc                                              20

<210> SEQ ID NO 6
<211> LENGTH: 22
<212> TYPE: DNA
<213> ORGANISM: Mice

<400> SEQUENCE: 6
gcctggtgcc gggaccgaag ta                                           22

<210> SEQ ID NO 7
<211> LENGTH: 20
<212> TYPE: DNA
<213> ORGANISM: Mice

<400> SEQUENCE: 7
gggctgaggc tgatccatta                                              20

<210> SEQ ID NO 8
<211> LENGTH: 25
<212> TYPE: DNA
<213> ORGANISM: Mice

<400> SEQUENCE: 8
tggcttgaca tgcagaaaac acctg                                        25

<210> SEQ ID NO 9
<211> LENGTH: 24
<212> TYPE: DNA
<213> ORGANISM: mice

<400> SEQUENCE: 9
tgaattccac agtcacttgg cttc                                         24

<210> SEQ ID NO 10
<211> LENGTH: 25
<212> TYPE: DNA
<213> ORGANISM: mice

<400> SEQUENCE: 10
gacacgtgat acaaagccca gggaa                                        25

<210> SEQ ID NO 11
<211> LENGTH: 21
<212> TYPE: DNA
<213> ORGANISM: mice

<400> SEQUENCE: 11
gtcaagggat ctactactgt g                                            21

<210> SEQ ID NO 12
<211> LENGTH: 34
<212> TYPE: DNA
<213> ORGANISM: mice

<400> SEQUENCE: 12
gagagaattc agagacaatc ccaagaacac cctg                              34

<210> SEQ ID NO 13
<211> LENGTH: 31
<212> TYPE: DNA
```

-continued

```
<213> ORGANISM: mice

<400> SEQUENCE: 13
gagagaattc tcctccagca cagcctacat g                              31

<210> SEQ ID NO 14
<211> LENGTH: 31
<212> TYPE: DNA
<213> ORGANISM: mice

<400> SEQUENCE: 14
gagagaattc ggctcccaat gacoctttct g                              31

<210> SEQ ID NO 15
<211> LENGTH: 21
<212> TYPE: DNA
<213> ORGANISM: mice

<400> SEQUENCE: 15
gtaagaatgg cctctccagg t                                         21

<210> SEQ ID NO 16
<211> LENGTH: 21
<212> TYPE: DNA
<213> ORGANISM: mice

<400> SEQUENCE: 16
gactcaatca ctaagacagc t                                         21

<210> SEQ ID NO 17
<211> LENGTH: 75
<212> TYPE: DNA
<213> ORGANISM: mice

<400> SEQUENCE: 17
agctgtatat ttctgtgcca gcagtgatgg ggactggggg ggcctcctat gaacagtact    60
tcggtcccgg cacca                                                    75

<210> SEQ ID NO 18
<211> LENGTH: 59
<212> TYPE: DNA
<213> ORGANISM: mice

<400> SEQUENCE: 18
agctgtatat ttctgtgcca gcagtgggac agttgaacag tacttcggtc ccgcacca     59

<210> SEQ ID NO 19
<211> LENGTH: 56
<212> TYPE: DNA
<213> ORGANISM: mice

<400> SEQUENCE: 19
agctgtatat ttctgtgcca gcggctccta tgaacagtac ttcggtcccg gcacca       56

<210> SEQ ID NO 20
<211> LENGTH: 62
<212> TYPE: DNA
<213> ORGANISM: mice

<400> SEQUENCE: 20
agctgtatat ttctgtgcca gccgacaggg gggctatgaa cagtacttcg gtcccggcac   60
ca                                                                  62
```

<210> SEQ ID NO 21
<211> LENGTH: 59
<212> TYPE: DNA
<213> ORGANISM: mice

<400> SEQUENCE: 21
agctgtatat ttctgtgcca gcagtgactg gggagaacag tacttcggtc ccggcacca        59

<210> SEQ ID NO 22
<211> LENGTH: 75
<212> TYPE: DNA
<213> ORGANISM: mice

<400> SEQUENCE: 22
atcagtgtac ttctgtgcca gcggtgatgg ggactggggg ggcctcctat gaacagtact        60
tcggtcccgg cacca        75

<210> SEQ ID NO 23
<211> LENGTH: 62
<212> TYPE: DNA
<213> ORGANISM: mice

<400> SEQUENCE: 23
atcagtgtac ttctgtgcca gcggtgggg gggctttgaa cagtacttcg gtcccggcac        60
ca        62

<210> SEQ ID NO 24
<211> LENGTH: 50
<212> TYPE: DNA
<213> ORGANISM: mice

<400> SEQUENCE: 24
atcagtgtac ttctgtgcca gcggcgaaca gtacttcggt cccggcacca        50

<210> SEQ ID NO 25
<211> LENGTH: 49
<212> TYPE: DNA
<213> ORGANISM: mice

<400> SEQUENCE: 25
atcagtgtac ttctgtgcca gcggtagccg tacttcggtc acggctcca        49

<210> SEQ ID NO 26
<211> LENGTH: 59
<212> TYPE: DNA
<213> ORGANISM: mice

<400> SEQUENCE: 26
atcagtgtac ttctgtgcca gccgtagctc ctatgaacag tacttcggtc ccggcacca        59

<210> SEQ ID NO 27
<211> LENGTH: 50
<212> TYPE: DNA
<213> ORGANISM: mice

<400> SEQUENCE: 27
atcagtgtat ttctgtgcca gcggtgaaca gtacttcggt cccggcacca        50

<210> SEQ ID NO 28
<211> LENGTH: 65
<212> TYPE: DNA

```
<213> ORGANISM: mice

<400> SEQUENCE: 28
atcagtgtac ttctgtgcca gcggtgacag ggactcctat gaacagtact tcggtcccgg    60
cacca                                                                65

<210> SEQ ID NO 29
<211> LENGTH: 75
<212> TYPE: DNA
<213> ORGANISM: mice

<400> SEQUENCE: 29
atctttgtac ttctgtgcca gcagtgatgg ggactggggg ggcctcctat gaacagtact    60
tcggtcccgg cacca                                                     75

<210> SEQ ID NO 30
<211> LENGTH: 65
<212> TYPE: DNA
<213> ORGANISM: mice

<400> SEQUENCE: 30
atctttgtac ttctgtgcca gcagtgatgc aggggcctat gaacagtact tcggtcccgg    60
cacca                                                                65

<210> SEQ ID NO 31
<211> LENGTH: 43
<212> TYPE: DNA
<213> ORGANISM: mice

<400> SEQUENCE: 31
atctttgtac ttctgtgcca gctgtacttc ggtcccggca cca                      43

<210> SEQ ID NO 32
<211> LENGTH: 59
<212> TYPE: DNA
<213> ORGANISM: mice

<400> SEQUENCE: 32
atctttgtac ttctgtgcca gcagtgatcc ctatgaacag tacttcggtc ccggcacca    59

<210> SEQ ID NO 33
<211> LENGTH: 62
<212> TYPE: DNA
<213> ORGANISM: mice

<400> SEQUENCE: 33
atctttgtac ttctgtgcca gcagtgattg ggcctatgaa cagtacttcg gtcccggcac    60
ca                                                                   62

<210> SEQ ID NO 34
<211> LENGTH: 57
<212> TYPE: DNA
<213> ORGANISM: mice

<400> SEQUENCE: 34
atctttgtac ttctgtgcca gcagtgacct atgaacagta cttcggtccc ggcacca      57
```